US012691004B2

(12) United States Patent　　　(10) Patent No.:　US 12,691,004 B2
Dabrowiak　　　　　　　　　　　　(45) Date of Patent:　　　Jul. 28, 2026

(54) SYSTEMS, DEVICES AND GARMENTS FOR SURFACE TEMPERATURE THERAPY OF A PATIENT

(71) Applicant: Zoll Circulation, Inc., San Jose, CA (US)

(72) Inventor: Jeremy Thomas Dabrowiak, Santa Clara, CA (US)

(73) Assignee: Zoll Circulation, Inc., San Jose, CA (US)

( * ) Notice: Subject to any disclaimer, the term of this patent is extended or adjusted under 35 U.S.C. 154(b) by 517 days.

(21) Appl. No.: 18/193,475

(22) Filed: Mar. 30, 2023

(65) Prior Publication Data

US 2023/0310206 A1　　Oct. 5, 2023

Related U.S. Application Data

(60) Provisional application No. 63/326,125, filed on Mar. 31, 2022.

(51) Int. Cl.
　　*A61F 7/00*　　　　(2006.01)
　　*A61F 7/02*　　　　(2006.01)
　　*A61F 7/12*　　　　(2006.01)
　　*D04B 1/16*　　　　(2006.01)
　　*D04B 1/22*　　　　(2006.01)
(52) U.S. Cl.
　　CPC .............. *A61F 7/0085* (2013.01); *D04B 1/16* (2013.01); *D04B 1/22* (2013.01); *A61F 2007/0008* (2013.01); *A61F 2007/0011* (2013.01); *A61F 2007/003* (2013.01); *A61F 2007/0054* (2013.01); *A61F 2007/0093* (2013.01); *A61F 2007/0234* (2013.01); *A61F*

*2007/0277* (2013.01); *A61F 2007/126* (2013.01); *D10B 2509/00* (2013.01)
(58) Field of Classification Search
　　CPC ................. A61F 2007/0054; A61F 2007/0056
　　See application file for complete search history.

(56) References Cited

U.S. PATENT DOCUMENTS 3,430,688　A　*　3/1969　Crocker ............... A41D 13/005
　　　　　　　　　　　　　　　　　　　174/15.1
11,116,657　B2　　9/2021　Dabrowiak et al.
(Continued)

FOREIGN PATENT DOCUMENTS

WO　　WO 2000/053992　　9/2000

OTHER PUBLICATIONS braincoolinc.com [online], "The IQool™ System," Aug. 7, 2020, retrieved on Jun. 1, 2023, retrieved from URL <https://braincoolinc.com/products/>, 4 pages.
(Continued)

*Primary Examiner* — Kaitlyn E Smith
(74) *Attorney, Agent, or Firm* — Fish & Richardson P.C.

(57)　　　　　　　　　　ABSTRACT

A conformable garment or device, for example, for performing heat exchange with a patient, includes one or more tubes. At least one of the one or more tubes has a lumen configured to receive fluid for flowing through the lumen of that tube to heat or cool the tube. The one or more tubes may be coupled to form a conformable fabric or material, such that the conformable fabric or material conforms to a non-planar shape. The conformable garment or device may conform to cover a particular portion of the patient's body to heat or cool the patient's body.

20 Claims, 20 Drawing Sheets

(56) References Cited

U.S. PATENT DOCUMENTS

| | | | |
|---|---|---|---|
| 11,185,440 B2 | 11/2021 | Dabrowiak et al. | |
| 2013/0138185 A1* | 5/2013 | Paxman | A61F 7/0085 |
| | | | 607/104 |
| 2018/0207024 A1* | 7/2018 | Dabrowiak | A61F 7/0085 |
| 2019/0133820 A1 | 5/2019 | Jacobsen et al. | |
| 2022/0313482 A1 | 10/2022 | Dabrowiak et al. | |

OTHER PUBLICATIONS dignicap.com [online], "The Dignicap Scalp Cooling System," Nov. 2019, retrieved on Jun. 1, 2023, retrieved from URL <https://dignicap.com/delta/>, 10 pages.

gentherm.com [online], "Patient Thermal Management Solutions," Gentherm, Oct. 2020, retrieved on Jun. 1, 2023, retrieved from URL <https://www.gentherm.com/sites/default/files/documents/Gentherm%20Magazine_Medical%2010-20%20small.pdf>, 48 pages.

Gori et al., "Inferring the thermal resistance and effective thermal mass distribution of a wall from in situ measurements to characterise heat transfer at both the interior and exterior surfaces," Energy and Buildings, Jan. 2017, 135:398-409.

Narayanan et al., "Automatic Machine Knitting of 3D Meshes," ACM Transactions on Graphics, Jan. 2018, retrieved from URL <https://textiles-lab.github.io/publications/2018-autoknit/>, vol. 1, No. 1, Article 1, 15 pages.

Raudensky et al., "Polymeric hollow fiber heat exchangers," Proceedings of the 14th International Conference on Simulation and Experiments in Heat Transfer and its Applications, 2016, pp. 95-105.

Sonder et al., "Efficacy of different cooling technologies for therapeutic temperature management: A prospective intervention study," Resuscitation, 2017, 124:14-20.

Sun et al., "Stretchable fabric generates electric power from woven thermoelectric fibers," Nature Communications, 2020, 11:572.

* cited by examiner

1000

1010

1300

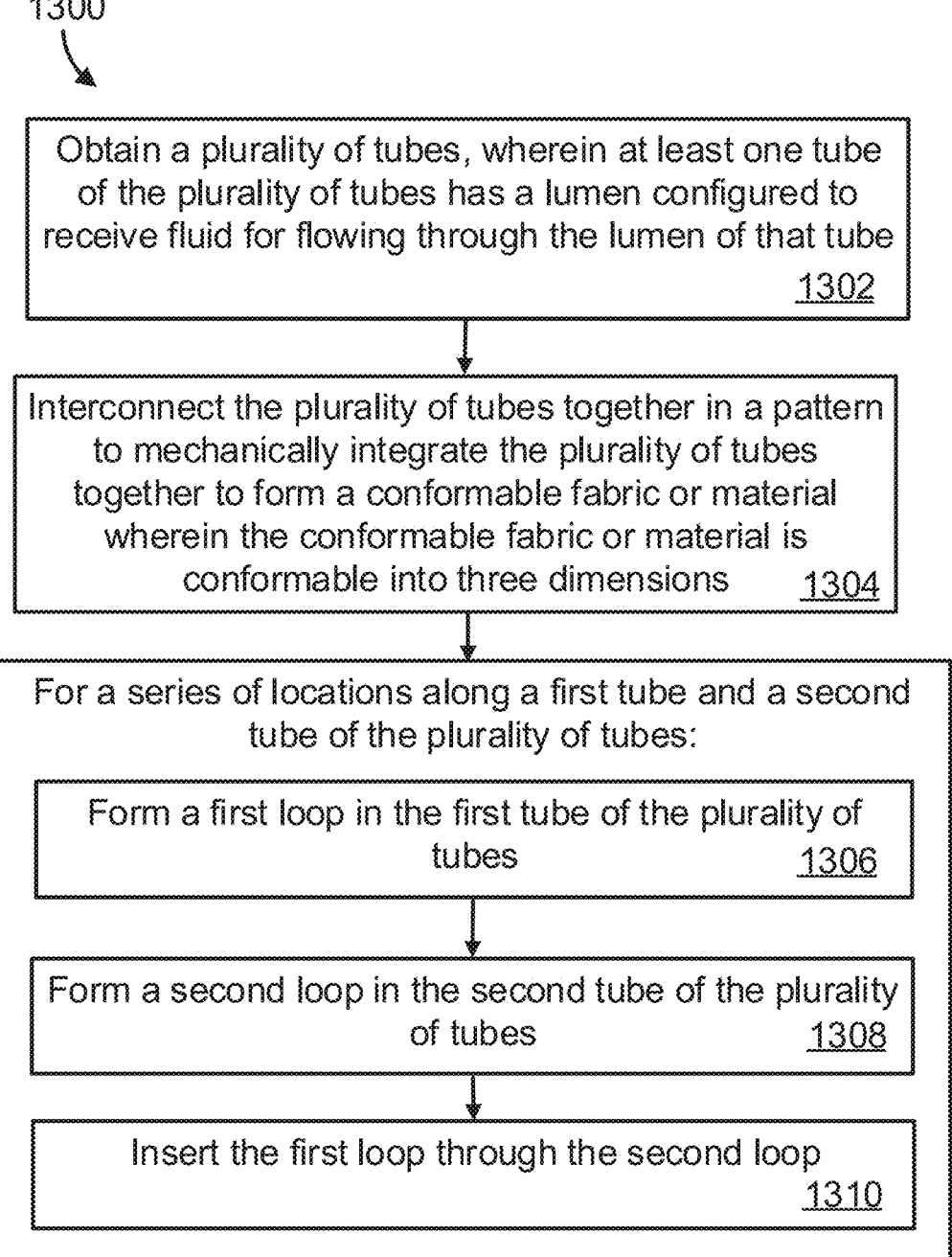

Obtain a plurality of tubes, wherein at least one tube of the plurality of tubes has a lumen configured to receive fluid for flowing through the lumen of that tube

1302

Interconnect the plurality of tubes together in a pattern to mechanically integrate the plurality of tubes together to form a conformable fabric or material wherein the conformable fabric or material is conformable into three dimensions    1304

For a series of locations along a first tube and a second tube of the plurality of tubes:

Form a first loop in the first tube of the plurality of tubes    1306

Form a second loop in the second tube of the plurality of tubes    1308

Insert the first loop through the second loop 1310

> Obtain a plurality of tubes, wherein at least one tube of the plurality of tubes has a lumen configured to receive fluid for flowing through the lumen of that tube
>
> 1402

> Couple the plurality of tubes together in a pattern to mechanically integrate the plurality of tubes together to form a conformable fabric or material wherein the conformable fabric or material is conformable into three dimensions     1404

> For a series of locations along a first tube and a second tube of the plurality of tubes:
>
> > Select first portions of a first tube of the plurality of tubes and second portions of the first tube, the first portions alternating with the second portions     1406
>
> > Couple third portions of a second tube of the plurality of tubes to the first portions of the first tube     1408
>
> > Couple fourth portions of a third tube of the plurality of tubes to the second portions of the first tube, the first tube being between the second tube and the third tube     1410

Obtain a plurality of tubes, wherein at least one tube of the plurality of tubes has a lumen configured to receive fluid for flowing through the lumen of that tube                    1502

Couple the plurality of tubes together in a pattern to mechanically integrate the plurality of tubes together to form a conformable fabric or material wherein the conformable fabric or material is conformable into three dimensions                    1504

For a series of locations along a first tube and a second tube of the plurality of tubes:

Adhere a first tube of the plurality of tubes to a second tube of the plurality of tubes at each location of a first set of locations on the first tube          1506

Adhere the first tube of the plurality of tubes is to a third tube of the plurality of tubes at each location of a second set of locations on the first tube, wherein the locations of the first set of locations are alternating with the locations of the second set of locations          1508

Obtain at least one tube, wherein the at least one tube has a plurality of portions and a lumen configured to receive fluid for flowing through the lumen of the at least one tube     1702

Interconnect the plurality of portions of the at least one tube with one another in a knit pattern to mechanically integrate the plurality of portions together to form a conformable fabric or material     1704

For a series of locations along a first portion and a second portion of the plurality of portions Form a first loop in the first portion
1706

Form a second loop in the second portion
1708

Insert the first loop through the second loop
1710

FIG. 17

SYSTEMS, DEVICES AND GARMENTS FOR SURFACE TEMPERATURE THERAPY OF A PATIENT

CLAIM OF PRIORITY

This application claims priority under 35 U.S.C. § 119(e) to U.S. Patent Application Ser. No. 63/326,125, filed on Mar. 31, 2022, the entire contents of which are hereby incorporated by reference.

BACKGROUND

In various clinical situations, it is desirable to warm, cool or otherwise control the body temperature of a subject. For example, hypothermia can be induced in humans and some animals for the purpose of protecting various organs and tissues (e.g., heart, brain, kidneys) against the effects of ischemic, anoxic or toxic insult. For example, animal studies and/or clinical trials suggest that mild hypothermia can have neuroprotective and/or cardioprotective effects in animals or humans who suffer from ischemic cardiac events (e.g., myocardial infarction, acute coronary syndromes, etc.), postanoxic coma after cardiopulmonary resuscitation, traumatic brain injury, stroke, subarachnoid hemorrhage, fever and neurological injury.

One method for inducing hypothermia is by intravascular or endovascular temperature management wherein a heat exchange catheter is inserted into a blood vessel and a thermal exchange fluid is circulated through a heat exchanger positioned on the portion of the catheter that is inserted in the blood vessel. As the thermal exchange fluid circulates through the catheter's heat exchanger, it exchanges heat with blood flowing past the heat exchanger in the blood vessel. Such technique can be used to cool the subject's flowing blood thereby resulting in a lowering of the subject's core body temperature to some desired target temperature. Endovascular temperature management is also capable of warming the body and/or of controlling body temperature to maintain a monitored body temperature at some selected temperature. If a controlled rate of re-warming or re-cooling from the selected target temperature is desired, that too can be accomplished by carefully controlling the amount of heat added or removed from the body and thereby controlling the temperature change of the patient.

Temperature management of the patient using intravascular or endovascular temperature management can be combined with or replaced by surface-based patient temperature management. A surface-based heat exchanger such as a pad or blanket is put in contact with the skin of the patient. The pad or blanket is heated or cooled for controlling the temperature of the patient to induce hypothermia or hyperthermia.

SUMMARY

This document describes systems, devices, and materials, e.g., for use in providing surface temperature management therapy to a patient. In certain implementations, the systems, devices or materials, may include one or more tubes that form a conformable heat exchange material or fabric. In certain implementations, the conformable material or fabric can be formed from the one or more tubes that are interlocked or otherwise coupled together, and no additional backing material or fabric is required. The one or more tubes can directly contact and/or conform to a surface of a patient for heat exchange with the patient. In some embodiments, the one or more tubes of the conformable material or fabric may be positioned on an additional material or fabric.

The one or more tubes may be connectable to a fluid source. In some implementations, the one or more tubes form a fluid loop when connected to the fluid source. The one or more tubes may be configured for a heat exchange fluid (e.g., water, gas, saline, coolant, etc.) to flow through the one or more tubes where the one or more tubes forms a heat exchange conformable fabric or material. The fluid can be heated or cooled by a heat exchanger, which can be remote from the heat exchange material or coupled to the heat exchange material. The heated or cooled fluid flows through the one or more tubes of the heat exchange conformable fabric or material to cause the heat exchange material to heat or cool an object that is contacting the heat exchange material.

The heat exchange fabric or material can be formed from the one or more tubes. For example, portions of a single tube may be interconnected with one another to form a conformable fabric or material and/or a plurality of different tubes may be interconnected with one another to form the conformable fabric or material. In certain implementations, a plurality of portions of a single tube can be looped together in a conformable knitted pattern. The conformable knitted pattern can include, for each portion, a plurality of loops that are interlocked with corresponding loops of one or more other portions. In certain implementations, a plurality of tubes can be looped together in a conformable knitted pattern. The conformable knitted pattern can include, for each tube, a plurality of loops that are interlocked with corresponding loops of one or more other tubes. The knitted pattern enables the heat exchange material that is formed from the one or more tubes to conform to convex three dimensional (3D) surfaces and also concave 3D surfaces to ensure maximum contact with the surface of the object being heated or cooled. The knitted pattern formed by the one or more tubes allows the heat exchange material to be conformable without stretching the one or more tubes, which may damage the one or more tubes. The knitted pattern of the one or more tubes enables the heat exchange material to be conformable without pinching the one or more tubes, which may restrict fluid flow in one or more of the tubes. For example, the heat exchange material can stretch in any dimension without stretching or pinching the one or more tubes, as described subsequently in greater detail.

In addition or alternatively to the knitted pattern described, the heat exchange material can be formed from one or more other patterns. In some implementations, a weave pattern is used to form the heat exchange material. In a weave pattern, the one or more tubes extend along two or more axes. Each tube, or portion of a single tube, extending along the first axis is interworked with the tubes or portions of a single tube extending along a second axis to form a conformable weave pattern. In some implementations, the one or more tubes of the heat exchange material include a braid pattern. In a braid pattern, the tubes or portions of a single tube are intertwined with one another to form a braid pattern.

A temperature management system can be connected to the heat exchange material for controlling temperature management of the patient for either heating or cooling the patient, maintaining a temperature of the patient, or a combination of heating, cooling, and maintaining the patient temperature. The temperature management system is configured to control a temperature of a patient's body using the heat exchange material.

The heat exchange material can be formed into a wearable heat exchange device or garment that is wearable by the patient. The garment can be positioned to snugly conform to curves or undulations of a surface of a patient. The heat exchange material is shaped to minimize overlapping portions of the fabric or material to maximize the cooling or warming power output (heat exchange power) of the heat exchange material for the patient. The heat exchange power output refers to the amount of cooling or heating performed (e.g., in Watts) on the patient by the heat exchange material. The higher contact percentage of the shaped heat exchange material with the patient (relative to unshaped materials such as pads, blankets, etc.) increases the heating or cooling efficiency of the heat exchange material. The fluid in the one or more tubes of the heat exchange material can be pumped more slowly though the one or more tubes, or heated or cooled relatively less, to achieve a comparatively same or greater heat exchange power output to the patient relative to a garment with many overlapping portions that do not directly contact the patient. The improved efficiency enables a greater maximum heating or cooling of the patient.

The heat exchange material, e.g., the one or more interconnected tubes, can be used to form many different kinds of heat exchange devices or garments. For example, the heat exchange material can form a hat or helmet that contacts a surface of the patient's head. The hat can be shaped to over any portion of the patient's head and face or cover the entire surface of the patient's head. The hat or helmet conforms to the head of the patient in a seamless manner without or with minimal overlapping portions or folds in the heat exchange material. The heat exchange material can form a neck wrap. The neck wrap can be integrated with the hat or helmet. The neck wrap can be integrated with a shirt or chest portion of the heat exchange material. The neck wrap forms a shape that conforms to the patient's neck and shoulders in a seamless manner without or with minimal overlapping portions of the heat exchange material or folds in the heat exchange material. The heat exchange material can form a shirt. The shirt can be sleeveless or have sleeves. The shirt can be sized to conform to the patient's chest, shoulders, armpits, and arms without having overlapping portions of the heat exchange material. The heat exchange material can form pants or shorts or a portion thereof. Other garments or portions thereof can be formed from the heat exchange material to over any particular portion of the patient in a seamless manner without having overlapping heat exchange material or folds in the heat exchange material.

The heat exchange material is connectable to a temperature management system that is configured to deliver temperature management treatment or therapy to the patient. The temperature management system is configured to monitor how the heat exchange device formed by the heat exchange material (such as a garment or portion thereof) is operating to control the temperature of the patient's body (also called treatment or heat exchange treatment). The temperature management system is configured to measure operational data representing operation of one or more hardware aspects of the temperature management system. The temperature management system is configured to measure patient data representing one or more physiological aspects of the patient during treatment of the patient e.g., patient temperature. The operational data and the patient data that are measured during treatment of the patient may be referred to as treatment data and the temperature management system is configured to control the temperature of the patient's body based on the operational and/or patient data. The temperature management system is configured to display, by a user interface, operational data of the temperature management system and patient data during treatment.

The heat exchange system is configured to be connected to pump fluid through the one or more tubes of the heat exchange material for exchanging heat with the patient. The pump speed and fluid temperature are configured based on the geometry of the heat exchange material. The geometry includes the type of interconnection of the tubes or portions of a single tube (e.g., knitting, braiding, etc.), a size of the heat exchange material, and a shape of the heat exchange material. The pump speed and fluid temperature are configured based on the target temperature of the patient. The heat exchange material is configured to maximize the heat exchange between the patient and the heat exchange fluid in the heat exchange material. The higher heat exchange efficiency allows for finer control of the patient temperature relative to a coarser control for a lower heat exchange efficiency. The higher heat exchange efficiency enables a faster heating or cooling rate, relative to a lower heat exchange rate for a less efficient heat exchange material.

The implementations described herein can provide one or more advantages. The material e.g., the one or more interconnected tubes, may be conformable to the contours of the patient's body. The interconnection pattern of the one or more tubes enables the material to conform to 3D contours without wrinkling, bunching, stretching, or pinching the one or more tubes of the material. The material may be shaped to contact the patient's body without substantially overlapping portions, which reduces heat exchange efficiency of an external heat exchange device comprising the material. The material may be configured to form an external heat exchange device that is configured to contact targeted portions of the patient in which the patient's vasculature is dense, close to the skin surface of the patient, or both. These regions have less tissue between the vasculature of the patient and the skin surface of the patient, which reduces thermal resistance between the vasculature of the patient and the heat exchange device. For example, the heat exchange device formed from the heat exchange material may be configured to conform to the patient's armpits and neck to form a continuous contact to the patient in these regions. The heat exchange device has increased heat exchange efficiency between the heat exchange device and the patient, relative to a heat exchange device that either does not conform to the skin of the patient, a device that has substantial overlapping portions of heat exchange material, or a device that is not targeted to particular regions of the patient's body. The increased thermal exchange efficiency results in an increased heat exchange rate between the patient and the heat exchange device when the pump speed and heat exchange fluid temperature are held constant. The reduced heat exchange with local tissue between the vasculature and the heat exchange device reduces the likelihood of the onset of shivering by the patient when cooling the patient. The heat exchange system can achieve higher overall heat exchange rates for either heating or cooling or both based on the increased heat exchange efficiency of the heat exchange device. The higher heat exchange rates may increase a heat exchange responsiveness of the heat exchange system, enabling finer temperature control of the patient temperature while using relatively less heating or cooling power than heat exchange systems using non-conformable pads.

The one or more tubes of the heat exchange material may be configured to receive a relatively high fluid pressure and a relatively low volume (flow rate) from a pump of the heat exchange system. The relatively high pressure and low flow rate are possible because of the relatively high heat exchange efficiency of the heat exchange material relative to a conventional external pad. The higher pressure helps prevent the tubes from kinking while the tubing has a relatively thin tube wall. The heat exchange material is thinner and has a smaller mass and is therefore lighter than a conventional heat exchange pad.

The implementations described herein can include one or more of the following embodiments.

In a general aspect, a system for providing external heat exchange to a patient, the system comprising: a heat exchange device for placement on the patient. The heat exchange device comprises a plurality of tubes, at least one tube of the plurality of tubes having a lumen configured to receive fluid for flowing through the lumen of that tube to heat the tube or cool the tube. The plurality of tubes may be interconnected such that the plurality of interconnected tubes is configured to conform into a three dimensional shape. The system comprises a control console comprising: a pump configured to pump fluid through the at least one tube of the plurality of tubes; a heat exchanger in thermal communication with the fluid for flowing through the lumen of the at least one tube of the plurality of tubes to heat or cool the at least one tube; a controller configured to control operation of the pump; and a user interface configured to receive inputs for controlling the pump and to display operational data for operation of the pump.

In some implementations, the system includes an intravenous catheter, wherein the heat exchange device comprises a fluid port for fluid communication with the intravenous catheter.

In some implementations, the system includes a cartridge configured to interface with the heat exchanger of the control console to exchange heat with the heat exchanger, the cartridge configured for fluid communication with the heat exchange device.

In some implementations, the plurality of interconnected tubes form a conformable fabric or material that is conformable to a three dimensional surface.

In some implementations, fluid flow in at least one tube of the plurality of tubes is configured to heat the tube or cool the at least one tube, and wherein the at least one tube is configured to perform heat transfer with an object in contact with the at least one tube, the heat transfer being based on the fluid flow through the at least one tube to heat or cool the at least one tube. In some implementations, the conformable fabric or material is comprised solely of the plurality of tubes.

In some implementations, the plurality of tubes are interconnected in a conformable knit pattern, the conformable knit pattern being stretchable at least along a first axis in a first dimension and at least along a second axis in a second dimension.

In some implementations, the knit pattern comprises a first knit pattern for a first region of the knit pattern and a second knit pattern for a second region of the knit pattern, the first knit pattern being different than the second knit pattern. In some implementations, wherein the knit pattern comprises: a first tube of the plurality of tubes, the first tube having a series of peaks and valleys; a second tube of the plurality of tubes, the second tube configured to wrap around the peaks of the first tube; and a third tube of the plurality of tubes, the third tube configured to wrap around the valleys of the first tube, wherein the first tube is between the second tube and the third tube. In some implementations, the knit pattern comprises one or more deformable cells configured to maintain an approximately constant perimeter during deformation. In some implementations, the knit pattern comprises interlocking loops of a plurality of sizes.

In some implementations, each tube of the plurality of tubes comprises one or more loops, wherein a first loop of a first tube of the plurality of tubes is interlocked with a second loop of a second tube of the plurality of tubes.

In some implementations, the first tube comprises a plurality of loops, the plurality of loops comprising loops having different sizes from one another.

In some implementations, the system comprises a pump tube that is configured to interface with the pump, the pump tube being connected to the at least one tube of the plurality of tubes in a closed loop. In some implementations, the pump is a peristaltic pump configured to drive fluid through the pump tube and the at least one tube of the plurality of tubes.

In some implementations, the plurality of interconnected tubes form a conformable fabric or material, wherein the fabric or material comprises edge pieces or the tubing itself forms edging of the fabric or material.

In a general aspect, a wearable heat-exchange device comprises a plurality of tubes, at least one tube of the plurality of tubes having a lumen configured to receive fluid, the at least one tube configured to allow for fluid flow through the lumen of that tube. The plurality of tubes are interconnected such that the plurality of interconnected tubes is configured to conform into a wearable three-dimensional shape.

In some implementations, the plurality of interconnected tubes form a conformable fabric or material that is conformable to a three dimensional surface.

In some implementations, fluid flow in at least one tube of the plurality of tubes is configured to heat or cool the at least one tube, and wherein the at least one tube is configured to perform heat transfer with an object in contact with the at least one tube, the heat transfer being based on the fluid flow through the at least one tube. In some implementations, the conformable fabric or material is comprised solely of the plurality of tubes. In some implementations, the plurality of tubes are interconnected in a conformable knit pattern, the conformable knit pattern being stretchable at least along a first axis in a first dimension and at least along a second axis in a second dimension.

In some implementations, wherein the conformable knit pattern comprises a first knit pattern for a first region of the conformable knit pattern and a second knit pattern for a second region of the conformable knit pattern, the first knit pattern being different than the second knit pattern. In some implementations, the conformable knit pattern comprises a first tube of the plurality of tubes, the first tube having a series of peaks and valleys; a second tube of the plurality of tubes, the second tube configured to wrap around the peaks of the first tube; and a third tube of the plurality of tubes, the third tube configured to wrap around the valleys of the first tube, wherein the first tube is between the second tube and the third tube.

In some implementations, the conformable knit pattern comprises one or more deformable cells configured to maintain an approximately constant perimeter during deformation.

In some implementations, the conformable knit pattern comprises interlocking loops of a plurality of sizes.

In some implementations, each tube of the plurality of tubes comprises one or more loops, wherein a first loop of a first tube of the plurality of tubes is interlocked with a second loop of a second tube of the plurality of tubes.

In some implementations, the first tube comprises a plurality of loops, the plurality of loops comprising loops having different sizes from one another.

In some implementations, the plurality of tubes are interconnected in a conformable braided pattern, the conformable braided pattern being stretchable at least along a first axis in a first dimension and at least along a second axis in a second dimension.

In some implementations, the plurality of tubes are interconnected in a woven pattern.

In some implementations, the woven pattern causes the plurality of tubes to retain a non-planar structure.

In some implementations, the plurality of tubes are interconnected based on coupling tubes of the plurality of tubes to one another with an adhesive.

In some implementations, a first tube of the plurality of tubes is adhered to a second tube of the plurality of tubes at each location of a first set of locations on the first tube, wherein the first tube of the plurality of tubes is coupled to a third tube of the plurality of tubes at each location of a second set of locations on the first tube, and wherein the locations of the first set of locations are alternating with the locations of the second set of locations.

In some implementations, the system comprises an input connected to the plurality of tubes, the input configured to receive fluid from a fluid source for inputting the fluid into at least one tube of the plurality of tubes, and an output configured to output fluid from the at least one tube of the plurality of tubes.

In some implementations, the plurality of interconnected tubes forms a heat exchanger configured for heat exchange with another object.

In some implementations, the plurality of interconnected tubes forms a garment that is wearable by a user. In some implementations, the garment is a heat exchange garment.

In some implementations, each tube of the plurality of tubes comprises a wall thickness between 0.05 and 0.1 inches, the wall thickness configured to prevent kinking of that tube or blockage of fluid flow in that tube.

In some implementations, each tube comprises polymeric material.

In some implementations, each tube has an inner diameter between 0.03 and 0.15 inches.

In some implementations, the plurality of interconnected tubes has a thickness of between 0.15 and 0.50 inches.

In some implementations, the system further comprises a backing layer coupled to the plurality of interconnected tubes, the backing layer comprising an insulating conformable fabric.

In some implementations, the fluid comprises a liquid.

In some implementations, the fluid comprises a gas.

In some implementations, the system further comprises a pump tube that is configured to interface with a pump, the pump tube being connected to the plurality of tubes in a closed loop. In some implementations, the pump backpressure is less than 60 pounds per square inch (psi) when producing a fluid flow rate adequate for clinically useful heat exchange.

In some implementations, the plurality of interconnected tubes is configured for a volume of less than 240 ml/minute, e.g., from 240 mL/minute to 120 mL/minute, of flow and a burst pressure of above 150 psi, e.g., from 150 to 250 psi, when producing a fluid flow rate adequate for clinically useful heat exchange.

In some implementations, the plurality of interconnected tubes is configured to deliver a cooling or warming power of 10-80 watts.

In some implementations, the system further comprises a port in at least one of the plurality of tubes, the port configured for interfacing with a draw line, a return line, or both the draw line and the return line of an intravenous catheter.

In some implementations, the plurality of interconnected tubes is configured for fluid throughput of at least 200-300 mL of fluid per minute.

In a general aspect, a conformable garment for performing heat exchange with a patient. The conformable garment comprises a plurality of tubes, at least one tube of the plurality of tubes having a lumen configured to receive fluid for flowing through the lumen of that tube to heat the tube or cool the tube. In some implementations, the plurality of tubes interconnected to form a conformable material or fabric, such that the conformable material or fabric conforms to a non-planar shape. In some implementations, the material or fabric conforms to cover a particular portion of the patient's body.

In some implementations, the garment is shaped to conform to a neck of the patient.

In some implementations, the garment comprises a single, non-folded layer shaped as a domed cap to cover a head of the patient.

In some implementations, the garment comprises a single, non-folded layer shaped to cover a shoulder and/or armpit of the patient.

In some implementations, the conformable material or fabric conforms to a non-planar shape based on varying a loop size or a number of loop neighbors for a knit pattern of the plurality of tubes.

In a general aspect, a method of forming a conformable material comprises obtaining a plurality of tubes, wherein at least one tube of the plurality of tubes has a lumen configured to receive fluid for flowing through the lumen of that tube; and coupling the plurality of tubes together in a knit pattern to mechanically integrate the plurality of tubes together to form the conformable material, wherein the conformable material is conformable into three dimensions.

In some implementations, the conformable material performs heat exchange with a patient.

In some implementations, coupling the plurality of tubes together in a knit pattern to mechanically integrate the plurality of tubes together comprises selecting first portions of a first tube of the plurality of tubes and second portions of the first tube, the first portions alternating with the second portions; coupling third portions of a second tube of the plurality of tubes to the first portions of the first tube; and coupling fourth portions of a third tube of the plurality of tubes to the second portions of the first tube; wherein the first tube is between the second tube and the third tube.

In some implementations, coupling the plurality of tubes together in a knit pattern if formed using one or more knitting needles.

In some implementations, coupling the plurality of tubes together in a knit pattern to mechanically integrate the plurality of tubes together comprises, for a series of locations along a first tube and a second tube of the plurality of tubes: forming a first loop in the first tube of the plurality of tubes; forming a second loop in the second tube of the plurality of tubes; and inserting the first loop through the second loop.

In some implementations, coupling the plurality of tubes together in a knit pattern to mechanically integrate the plurality of tubes together comprises: adhering or fastening a first tube of the plurality of tubes to a second tube of the plurality of tubes at each location of a first set of locations on the first tube; and adhering or fastening the first tube of the plurality of tubes is to a third tube of the plurality of tubes at each location of a second set of locations on the first tube, wherein the locations of the first set of locations are alternating with the locations of the second set of locations.

In a general aspect, a device comprises a plurality of tubes, at least one tube of the plurality of tubes having a lumen configured to receive fluid, the at least one tube configured to allow for fluid flow through the lumen of that tube; the plurality of tubes being interconnected, such that the plurality of interconnected tubes is configured to conform into a three dimensional shape.

In some implementations, the plurality of interconnected tubes form a wearable heat exchange device conformable to a three dimensional surface.

In some implementations, fluid flow in at least one tube of the plurality of tubes is configured to heat or cool the at least one tube, and wherein the at least one tube is configured to perform heat transfer to an object in contact with the at least one tube, the heat transfer being based on the fluid flow through the at least one tube to heat or cool the at least one tube.

In some implementations, the wearable heat exchange device is comprised solely of the plurality of tubes.

In some implementations, the plurality of tubes are interconnected in a conformable knit pattern being stretchable at least along a first axis in a first dimension and at least along a second axis in a second dimension.

In some implementations, the knit pattern comprises a first knit pattern for a first region of the knit pattern and a second knit pattern for a second region of the knit pattern, the first knit pattern being different than the second knit pattern.

In some implementations, the knit pattern comprises: a first tube of the plurality of tubes, the first tube having a series of peaks and valleys; a second tube of the plurality of tubes, the second tube configured to wrap around the peaks of the first tube; and a third tube of the plurality of tubes, the third tube configured to wrap around the valleys of the first tube, wherein the first tube is between the second tube and the third tube.

In some implementations, the knit pattern comprises one or more deformable cells configured to maintain an approximately constant perimeter during deformation.

In some implementations, the knit pattern comprises interlocking loops of a plurality of sizes.

In some implementations, each tube of the plurality of tubes comprises one or more loops, wherein a first loop of a first tube of the plurality of tubes is interlocked with a second loop of a second tube of the plurality of tubes.

In some implementations, the first tube comprises a plurality of loops, the plurality of loops comprising loops having different sizes from one another.

In a general aspect, a system for providing external heat exchange to a patient. The system comprises a heat exchange device for placement on the patient, the heat exchange device comprising: at least one tube, the at least one tube having a lumen configured to receive fluid for flowing through the lumen of that tube to heat the tube or cool the tube; the at least one tube having a plurality of portions that are interconnected with one another and configured to conform into a three dimensional shape; and a control console comprising: a pump configured to pump fluid through the at least one tube; a heat exchanger in thermal communication with the fluid for flowing through the lumen of the at least one tube to heat or cool the at least one tube; a controller configured to control operation of the pump; and a user interface configured to receive inputs for controlling the pump and to display operational data for operation of the pump.

In some implementations, each portion of the plurality of portions is formed into a series of loops, and wherein, for each loop of the series of loops of a first portion of the plurality of portions, that loop is looped around a base of a corresponding loop of a second portion of the plurality of portions, the first and second portions forming a knitted pattern.

In some implementations, the system includes an intravenous catheter, wherein the heat exchange device comprises a fluid port for fluid communication with the intravenous catheter.

In some implementations, the system includes a cartridge configured to interface with the heat exchanger of the control console to exchange heat with the heat exchanger, the cartridge configured for fluid communication with the heat exchange device.

In some implementations, the at least one tube forms a conformable fabric or material that is conformable to a three dimensional surface.

In some implementations, fluid flow in the at least one tube is configured to heat or cool the at least one tube, and wherein the at least one tube is configured to perform heat transfer with an object in contact with the at least one tube, the heat transfer being based on the fluid flow through the at least one tube to heat or cool the at least one tube.

In some implementations, the conformable fabric or material is comprised solely of the at least one tube.

In some implementations, the conformable fabric or material further comprises edge pieces or the at least one tube itself forms edging of the conformable fabric or material.

In some implementations, the plurality of portions of the at least one tube are interconnected with one another in a conformable knit pattern that is stretchable at least along a first axis in a first dimension and at least along a second axis in a second dimension.

In some implementations, the conformable knit pattern comprises a first knit pattern for a first region of the conformable knit pattern and a second knit pattern for a second region of the conformable knit pattern, the first knit pattern being different than the second knit pattern.

In some implementations, the conformable knit pattern comprises: a first portion of the plurality of portions, the first portion having a peak and valley; a second portion of the plurality of portions, the second portion configured to wrap around the peak of the first portion; and a third portion of the plurality of portions, the third portion configured to wrap around the valley of the first portion, wherein the first portion is between the second portion and the third portion.

In some implementations, the conformable knit pattern comprises one or more deformable cells configured to maintain an approximately constant perimeter during deformation.

In some implementations, the conformable knit pattern comprises interlocking loops of a plurality of sizes.

In some implementations, each portion of the plurality of portions comprises one or more loops, wherein a first loop of a first portion of the plurality of portions is interlocked with a second loop of a second portion of the plurality of portions.

In some implementations, the first portion comprises a plurality of loops, the plurality of loops comprising loops having different sizes from one another.

In some implementations, the system includes a pump tube that is configured to interface with the pump, the pump tube being connected to the at least one tube in a closed loop.

In some implementations, the pump is a peristaltic pump configured to drive fluid through the pump tube and the at least one tube.

In some implementations, each portion of the plurality of portions is formed into a series of loops, and wherein, for each loop of the series of loops of a first portion of the plurality of portions, that loop is looped around a base of a corresponding loop of a second, different portion of the tube, the first and second portions forming a knitted pattern.

In a general aspect, a wearable heat-exchange device comprises at least one tube having a lumen configured to receive fluid, the at least one tube configured to allow for fluid flow through the lumen of that tube; the at least one tube having a plurality of portions that are interconnected with one another and configured to conform into a wearable three dimensional shape.

In some implementations, each portion of the plurality of portions is formed into a series of loops, and wherein, for each loop of the series of loops of a first portion of the plurality of portions, that loop is looped around a base of a corresponding loop of a second portion of the plurality of portions, the first and second portions forming a knitted pattern.

In some implementations, the at least one tube having a plurality of interconnected portions forms a fabric or material that is conformable to a three dimensional surface.

In some implementations, fluid flow in the at least one tube is configured to heat or cool the at least one tube, and wherein the at least one tube is configured to perform heat transfer with an object in contact with the at least one tube, the heat transfer being based on the fluid flow through the at least one tube.

In some implementations, the fabric or material is comprised solely of the at least one tube.

In some implementations, the plurality of portions are interconnected in a conformable knit pattern that is stretchable at least along a first axis in a first dimension and at least along a second axis in a second dimension.

In some implementations, the conformable knit pattern comprises a first knit pattern for a first region of the conformable knit pattern and a second knit pattern for a second region of the conformable knit pattern, the first knit pattern being different than the second knit pattern.

In some implementations, the conformable knit pattern comprises: a first portion of the plurality of portions, the first portion having a series of peaks and valleys; a second portion of the plurality of portions, the second portion configured to wrap around the peaks of the first tube; and a third portion of the plurality of portions, the third portion configured to wrap around the valleys of the first portion, wherein the first portion is between the second portion and the third portion.

In some implementations, the conformable knit pattern comprises one or more deformable cells configured to maintain an approximately constant perimeter during deformation.

In some implementations, the conformable knit pattern comprises interlocking loops of a plurality of sizes.

In some implementations, each portion of the plurality of portions comprises one or more loops, wherein a first loop of a first portion of the plurality of portions is interlocked with a second loop of a second portion of the plurality of portions.

In some implementations, the first portion comprises a plurality of loops, the plurality of loops comprising loops having different sizes from one another.

In some implementations, the plurality of portions are interconnected in a conformable braided pattern that is stretchable at least along a first axis in a first dimension and at least along a second axis in a second dimension.

In some implementations, the plurality of portions are interconnected in a woven pattern.

In some implementations, the woven pattern causes the at least one tube having a plurality of interconnected portions to retain a non-planar structure.

In some implementations, the plurality of portions are interconnected based on coupling portions of the plurality of portions to one another with an adhesive.

In some implementations, a first portion of the plurality of portions is adhered to a second portion of the plurality of portions at each location of a first set of locations on the first portion, wherein the first portion of the plurality of portions is coupled to a third portion of the plurality of portions at each location of a second set of locations on the first portion, and wherein the locations of the first set of locations are alternating with the locations of the second set of locations.

In some implementations, the system includes an input connected to the at least one tube, the input configured to receive fluid from a fluid source for inputting the fluid into the least one tube; and an output configured to output fluid from the at least one tube. In some implementations, the at least one tube having a plurality of interconnected portions forms a heat exchanger configured for heat exchange with another object.

In some implementations, the at least one tube having a plurality of interconnected portions forms a garment that is wearable by a user. In some implementations, the garment is a heat exchange garment.

In some implementations, the at least one tube comprises a wall thickness between 0.05 and 0.1 inches, the wall thickness configured to prevent kinking of the at least one tube or blockage of fluid flow in the at least one tube.

In some implementations, the at least one tube comprises polymeric material.

In some implementations, the at least one tube has an inner diameter between 0.03 and 0.15 inches.

In some implementations, the at least one tube having a plurality of interconnected portions has a thickness of between 0.15 and 0.50 inches.

In some implementations, the system includes a backing layer coupled to the at least one tube having a plurality of interconnected portions, the backing layer comprising an insulating conformable fabric.

In some implementations, the fluid comprises a liquid.

In some implementations, the fluid comprises a gas.

In some implementations, the system comprises a pump tube that is configured to interface with a pump, the pump tube being connected to the at least one tube in a closed loop.

In some implementations, the pump backpressure is less than 60 pounds per square inch (psi) when producing a fluid flow rate adequate for clinically useful heat exchange.

In some implementations, the at least one tube has a plurality of interconnected portions is configured for a volume of less than 240 mL/minute of flow and a burst pressure of above 150 psi when producing a fluid flow rate adequate for clinically useful heat exchange.

In some implementations, the plurality of interconnected portions is configured to deliver a cooling or warming power of 10-80 watts.

In some implementations, the system includes a port in the at least one tube, the port configured for interfacing with a draw line, a return line, or both the draw line and the return line of an intravenous catheter.

In some implementations, the plurality of interconnected portions is configured for fluid throughput of at least 200-300 mL of fluid per minute.

In a general aspect, a garment for performing heat exchange with a patient. The garment includes at least one tube having a lumen configured to receive fluid for flowing through the lumen of the at least one tube to heat or cool the at least one tube, the at least one tube having a plurality of portions that are interconnected with one another and configured to conform to a non-planar shape, wherein the plurality of interconnected portions conform to cover a particular portion of the patient's body.

In some implementations, each portion of the plurality of portions is formed into a series of loops, and wherein, for each loop of the series of loops of a first portion of the plurality of portions, that loop is looped around a base of a corresponding loop of a second portion of the plurality of portions, the first and second portions forming a knitted pattern.

In some implementations, the garment is shaped to conform to a neck of the patient.

In some implementations, the garment comprises a single, non-folded layer shaped as a domed cap to cover a head of the patient.

In some implementations, the garment comprises a single, non-folded layer shaped to cover a shoulder and/or armpit of the patient.

In some implementations, the plurality of interconnected portions conforms to a non-planar shape based on varying a loop size or a number of loop neighbors for a knit pattern of the plurality of interconnected portions of the at least one tube.

In a general aspect, a method of forming a conformable fabric comprises obtaining at least one tube, wherein the at least one tube has a plurality of portions and a lumen configured to receive fluid for flowing through the lumen of the at least one tube; and interconnecting the plurality of portions of the at least one tube with one another in a knit pattern to mechanically integrate the plurality of portions together, wherein the plurality of interconnected portions is conformable into three dimensions.

In some implementations, each portion of the plurality of portions is formed into a series of loops, and wherein, for each loop of the series of loops of a first portion of the plurality of portions, that loop is looped around a base of a corresponding loop of a second portion of the plurality of portions, the first and second portions forming a knitted pattern.

In some implementations, the at least one tube performs heat exchange with a patient.

In some implementations, coupling the plurality of portions together in a knit pattern to mechanically integrate the plurality of portions together comprises: selecting a first portion and second portion of the plurality of portions, the first portion alternating with the second portion; coupling a third portion to the first portion; and coupling a fourth portion to the second portion; wherein the first portion is between the second portion and the third portion.

In some implementations, coupling the plurality of portions of the at least one tube together in a knit pattern if formed using one or more knitting needles.

In some implementations, coupling the plurality of portions of the at least one tube together in a knit pattern to mechanically integrate the plurality of portions together comprises: for a series of locations along a first portion and a second portion of the plurality of portions: forming a first loop in the first portion; forming a second loop in the second portion; and inserting the first loop through the second loop.

In some implementations, coupling the plurality of portions of the at least one tube together in a knit pattern to mechanically integrate the plurality of portion together comprises: adhering or fastening a first portion to a second portion at each location of a first set of locations on the first portion; and adhering or fastening the first portion to a third portion at each location of a second set of locations on the first portion; wherein the locations of the first set of locations are alternating with the locations of the second set of locations.

In a general aspect, a device comprises at least one tube having a lumen configured to receive fluid, the at least one tube configured to allow for fluid flow through the lumen of the at least one tube; the at least one tube having a plurality of portions that are interconnected with one another and configured to conform into a three dimensional shape.

In some implementations, each portion of the plurality of portions is formed into a series of loops, and wherein, for each loop of the series of loops of a first portion of the plurality of portions, that loop is looped around a base of a corresponding loop of a second portion of the plurality of portions, the first and second portions forming a knitted pattern.

In some implementations, the plurality of interconnected portions is a wearable heat exchange device conformable to a three dimensional surface.

In some implementations, fluid flow in the at least one tube is configured to heat or cool the at least one tube, and wherein the plurality of interconnected portions is configured to perform heat transfer to an object in contact with the plurality of interconnected portions, the heat transfer being based on the fluid flow through the at least one tube to heat or cool the at least one tube.

In some implementations, the plurality of interconnected portions is comprised solely of the at least one tube.

In some implementations, the plurality of portions of the at least one tube are interconnected in a knit pattern that enables the plurality of interconnected portions to stretch at least along a first axis in a first dimension and at least along a second axis in a second dimension.

In some implementations, the knit pattern comprises a first knit pattern for a first region of the plurality of interconnected portions and a second knit pattern for a second region of the plurality of interconnected portions, the first knit pattern being different than the second knit pattern.

In some implementations, the knit pattern comprises: a first portion of the plurality of portions, the first portion having a series of peaks and valleys; a second portion of the plurality of portions, the second portion configured to wrap around the peaks of the first tube; and a third portion of the plurality of portions, the third portion configured to wrap around the valleys of the first portion, wherein the first portion is between the second portion and the third portion.

In some implementations, the knit pattern comprises one or more deformable cells configured to maintain an approximately constant perimeter during deformation.

In some implementations, the knit pattern comprises interlocking loops of a plurality of sizes.

In some implementations, each portion of the plurality of interconnected portions comprises one or more loops, wherein a first loop of a first portion is interlocked with a second loop of a second portion.

In some implementations, the at least one tube comprises a plurality of loops, the plurality of loops comprising loops having different sizes from one another.

In some implementations, the plurality of tubes being interconnected comprises portions of a tube being coupled to respective portions of one or more other tubes in regular or semi-regular pattern.

In a general aspect, a system provides external heat exchange to a patient. The system comprises a heat exchange device for placement on the patient, the heat exchange device comprising: a conformable fabric comprising: a plurality of tubes, at least one tube of the plurality of tubes having a lumen configured to receive fluid for flowing through the lumen of that tube to heat the tube or cool the tube; the plurality of tubes interconnected to form the conformable fabric, such that the conformable fabric is configured to conform into a three dimensional shape; and a control console comprising: a pump configured to pump fluid through the at least one tube of the plurality of tubes of the conformable fabric; a heat exchanger in thermal communication with the fluid for flowing through the lumen of the at least one tube of the plurality of tubes to heat or cool the at least one tube; a controller configured to control operation of the pump; and a user interface configured to receive inputs for controlling the pump and to display operational data for operation of the pump.

In a general aspect, a wearable heat-exchange device comprises a conformable fabric that is configured for fluid flow. The conformable fabric comprises a plurality of tubes, at least one tube of the plurality of tubes having a lumen configured to receive fluid, the at least one tube configured to allow for fluid flow through the lumen of that tube, the plurality of tubes interconnected to form the conformable fabric, such that the conformable fabric is configured to conform into a three-dimensional shape.

Computer program code may be provided to implement any of the aspects.

For example, there may be provided a non-transitory computer readable medium comprising computer program code that is configured to cause at least one processor to perform any of the method steps described with respect to the different aspects. It will be appreciated that an implementation described with respect to one aspect may be combined with a different aspect. In general it will be appreciated that the at least one sensor may be provided separately from a system of an aspect and the system may instead be configured to receive data from the sensor. This is particularly applicable in the case that the at least one sensor is a consumable item that may be provided separately to the remainder of the system.

The details of one or more embodiments are set forth in the accompanying drawings and the description below. Other features and advantages will be apparent from the description and drawings, and from the claims.

BRIEF DESCRIPTION OF THE DRAWINGS

FIG. 13 shows a flow diagram including an example process for forming a heat exchange material.

FIG. 14 shows a flow diagram including an example process for forming a heat exchange material.

FIG. 15 shows a flow diagram including an example process for forming a heat exchange material.

FIG. 17 shows a flow diagram including an example process for forming a heat exchange material.

DETAILED DESCRIPTION

Figures 1A, 1B, 1C:
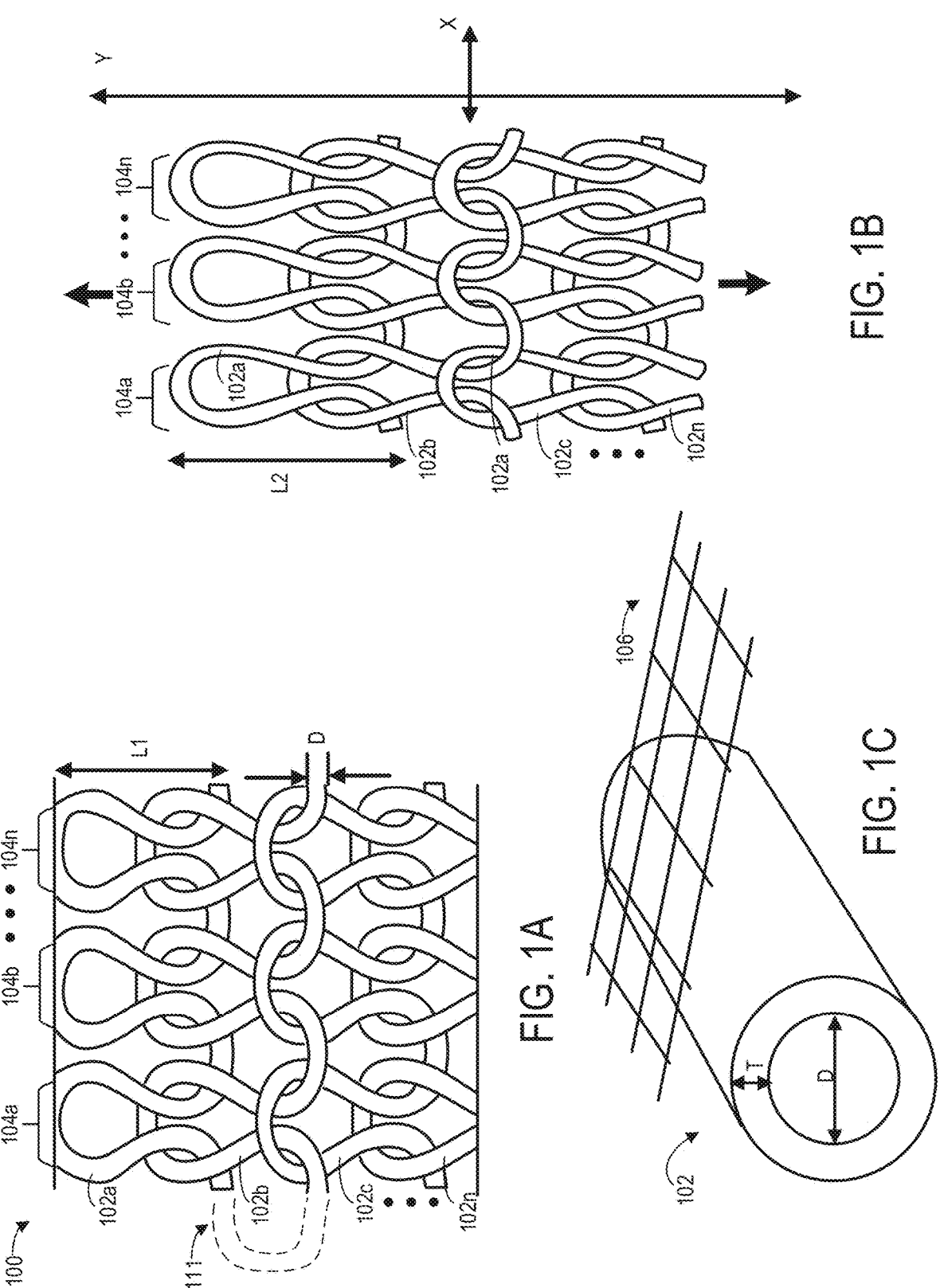
FIG. 1A shows an example of a material having a knitted pattern.
FIG. 1B shows an example of the material of FIG. 1A.
FIG. 1C shows a cross-section of a tube of material of FIG. 1A.

FIG. 1A shows an example of a conformable material 100 having a knitted pattern. The material 100 may form a heat exchange device configured to transfer heat to a patient for heat exchange therapy and temperature management of the patient. The material 100 includes one or more tubes. For example, a single tube having a plurality of tube portions or segments or a plurality of tubes (102a, 102b, 102c . . . 102n) may form a conformable material or fabric. While four rows of tubes or tube portions 102a-n are shown, the material 100 can include any number of tubes, e.g., the material may include a single tube 102. In certain implementations, the one or more tubes of the material 100 may form a conformable fabric or material without additional fabrics or materials. In other words, the material 100 may be formed only from the one or more tubes 102 themselves, rather than the tubes being embedded in another fabric or material or otherwise coupled to another fabric or material. The one or more tubes may be arranged to form interlocking/interconnected portions or otherwise coupled portions that, together, enable the one or more tubes to form a conformable heat exchange device, garment, fabric or material.

The one or more tubes 102 are connectable to a fluid source (subsequently described). In some implementations, the one or more tubes form a fluid loop when connected to the fluid source. The one or more tubes 102 are configured for a heat exchange fluid (e.g., water, gas, saline, coolant, etc.) to flow through the one or more tubes. The fluid can be heated or cooled by a heat exchanger, which can be remote from the heat exchange material or coupled to the heat exchange material. The heated or cooled fluid flows through the one or more tubes 102 of the material 100 to cause the material to heat or cool an object that is contacting the material. In some implementations, the knitted one or more tubes 102 form a garment. The material 100 can be used for any exchange process, such as gas exchange, heat exchange, and so forth, depending on the material used to form the one or more tubes 102. Walls of the one or more tubes form a transfer medium/membrane.

The material is formed by the plurality of tubes 102 being interconnected with one another, or a plurality of portions of a single tube being interconnected with one another. Each of the one or more tubes 102 may form a series of loops 104, such as loops 104a, 104b . . . 104n. The portions of a single tube or a plurality of tubes 102 can be looped together in a knitted pattern to form a conformable kitted pattern or material or fabric. In certain implementations, the knitted pattern can include, for each tube 102a-n, a plurality of loops 104a-n that are interlocked with corresponding loops of one or more other tubes. For example, tube 102b is looped around tube 102a, tube 102c is looped around tube 102b, and so forth. Each loop 104a may be looped around the base of the corresponding loop of a different tube to create the knitted pattern. In certain implementations, the one or more tubes 102 are a single tube that is used to form the knitted pattern. FIG. 1A may also represent a single tube 102 that is formed into loops by folding or switching the tube back (e.g., shown with dashed lines 111) and forth to form each of loops 104a-n, where, for example, the tubes 102a-c can each be segments or portions of a single tube.

The knitted pattern is shown in a relaxed state in FIG. 1A. The loops 104 enable the material 100 to stretch in any axis, such as the first axis (labeled X), a second axis (labeled Y), or a combination of both the first and second axes. The first and second axes in this example are orthogonal to one another. The knitted one or more tubes 102 form a sheet of the material 100. As subsequently described, the sheet of the material 100 can be formed into any shape as desired. For example, a number of garment shapes are formable using the material 100 in heat exchange applications to provide heat exchange to target regions of the patient's body, such as the armpits, neck, etc. as subsequently described.

FIG. 1B shows the material 100 in a stretched state. The material 100 may stretch to conform to a surface, such a patient's skin. The loops 104 are stretched from length L1 in the relaxed state to length L2 in the stretched state, where L2 is greater than L1. The loops 104 thus stretch in size, rather than tensioning the walls of the one or more tubes, thereby stretching e.g., without inducing stress and resulting strain on the tube walls or with reduced stress and strain. The walls of one or more tubes 102 are not stressed when the material 102 is stretched to conform to a curved surface.

The knitted pattern enables the material 100 that is formed from the one or more tubes to conform to convex three dimensional (3D) surfaces and also concave 3D surfaces to ensure maximum contact with the surface of the object being heated or cooled. The knitted pattern of the one or more tubes 102 enables the material 100 to be conformable without stretching the tubes, which may damage the one or more tubes. The knitted pattern of the one or more tubes 102 enables the material 100 to be conformable without pinching the one or more tubes 102, which may restrict fluid flow in one or more of the tubes. For example, the material 100 can stretch in any dimension without stretching or pinching the one or more tubes, as described subsequently in greater detail.

The knitted one or more tubes 102 form a fabric or material 100. The material 100 can include only the one or more tubes 102 that are interconnected with itself or one another. The one or more tubes 102 form the structure of the material 100. When used to provide heat exchange with the surface of a patient, the skin of the patient evens out the gaps in the tubing 102 (e.g., in the loops 104) to result in an effectively uniform heat exchange with the patient.

In some implementations, another material can be added to the material 100. For example, a cover 106 can be applied to the one or more tubes 102 of the material 100, either individually or covering the material 100 over a plurality of the tubes 102. The cover 106 can be configured to improve contact of the material 100 with a skin of the patient. For example, the cover material can include fabrics such as compression fabrics, e.g., spandex, and neoprene/fabric composites, to press the material 100 onto the patient's skin to enhance heat exchange.

In some implementations, the cover fabric can be configured to hold the material 100 in place on the patient to maximize heat exchange with the patient. The cover fabric can include a compressive material. The cover fabric can be configured to reduce parasitic losses (e.g., to the air or to objects other than the patient). The cover fabric can include an insulating layer configured to reduce heat exchange with the ambient environment and to limit condensation.

The material 100 can include a variable pattern of the loops in size ratio and/or in a number of linked neighbors for the loops. For example, the loops can be linked with two neighbors, five neighbors, or another number of neighbors to knit any arbitrary 3D shape. For example, ratios for rows to columns can include ratios of 5:4, 3:2, 5:1, 2:1, or other ratios. Furthermore, the element size (e.g., size of loops 104) can be varied to further generate natural curves in the material 100 for conforming to a particular surface (e.g., a head, shoulder, neck, etc. of a patient). For example, in a planar material, each loop in a row connects with the same number of loops (e.g. 1 or 2) in the row above as to the row below. A loop could connect to two loops in the row below and two loops in the row above. In other words, the ratio of loops below to loops above is 1:1. In a non-planar material, a loop can connect to three loops in the row below and two loops in the row above. Its ratio of loops below to loops above is something other than 1:1; in this case 3:2. This ratio can be varied in an irregular manner to create an arbitrary material, garment or fabric topology which may be designed to match human anatomy in a region of interest.

The material 100 is thus not only formable as a sheet of material but also a shaped form that can conform to a particular curved (3D or non-planar) surface (such as a patient's head, neck, armpit, etc.). This enables more variable shapes than simple shapes formed from weave patterns, such as a cone, or flat sheets that are folded into 3D shapes. The knitted configuration of the material 100 enables more flexibility than a corresponding woven structure because knitting produces cells with an approximately constant perimeter, as shown in the comparison of FIG. 1A to FIG. 1B. For example, a cell with a perimeter of 12 units could be 3 wide×4 tall. The cell can be deformed to be 4 wide×3 tall (e.g., L1 is 3 units, and L2 is 4 units). Deforming the cell in this way so flexes the tubing 102 but does not elongate (stretch) the one or more tubes 102.

The material 100 is configured to conform to contours of the patient. For example, the material 100 can be variably patterned or shaped to form a garment that conforms to a target anatomy, as subsequently described For example, the material 100 can be configured for placement on the neck of the patient for improved heat exchange with neck vasculature. In this way, areas of the patient's body with low thermal resistance are specifically targeted, and other areas of the patient's body are avoided, resulting a more efficient heat transfer rate.

FIG. 1C shows a cross-section of a tube 102 of material 100 of FIG. 1A. The tube 102 has an interior diameter D and a wall thickness T. As previously described, the knitted pattern of the material 100 enables the material to conform to curved surfaces (or be curved in manufacture) without narrowing the interior diameter D of the tube 102, which would restrict flow of heat exchange fluid or gas exchange. The dimensions of the tube thickness T and the diameter D can vary depending on the desired heat transfer rate and particular implementation of the material 100. Example dimensions of tubing thickness, diameter, overlap percentage, and so forth described below.

The internal diameter D of the one or more tubes 102 can be uniform throughout the material 100. In an example, the diameter of the tube 102 can be between 0.030 inches and 0.15 inches. The particular diameter selected can vary depending on the tube interconnection used, the thickness T of the tube wall, the tubing material, and the size of the heat exchange material 100. In some implementations, the tube wall is between 0.05 and 0.07 inches thick. However, the diameter D and tube wall thickness T can vary between 0.01 inches and 1.00 inches. The parameters D and T also depend on a flow pressure/volume target and a desired rate of heat exchange. In examples where a plurality of tubes are used, the tubes may have identical or different diameters.

Where a plurality of tubes are used, the tubes can be plumbed in parallel fluid loops with one another such that the pump pushes fluid through the tubes in parallel. Parallel tubes can be constructed by incorporating a divergent (or upstream) manifold which separates the flow into multiple parallel streams, and a convergent (or downstream) manifold which recombines the streams. In some implementations, the number of tubes is 1, such that there are no tubes in parallel but a single tube that is knitted into a pattern. For example, different portions of the tube can be formed into loops as previously described. Different portions of the tube can be arranged in a parallel configures to one another. In an example, each of the tubes is a discrete fluid loop in which the plurality of tubes are not in fluid communication with one another. In another example, the tubes are mechanically interconnected to form the conformable material or fabric, but are in fluid communication with one another.

A minimum bend radius correlates with how tight the knit pattern can be. Certain implementations may have one or more tubes with a smaller tubing bend radius providing smaller gaps where the skin is not covered by tubing. A larger tubing bend radius leads to larger stitches, which may leave larger gaps where the skin is not covered by tubing and thereby is not exchanging heat. Moderate gaps (up to 0.25") are unlikely to have significant impact on heat transfer as the patient's tissue becomes a limiting factor in overall heat exchange.

A rated pressure of the tubing should not be exceeded by the heat exchange system as backpressure is generated by pumping heat exchange fluid through the tubing. If too high of a backpressure is generated for a given tubing, then the backpressure may be reduced by either reducing the fluid flow rate, or by ganging multiple tubes in parallel. Ganging (or manifolding) multiple tubes in parallel has the advantage of reducing the flow velocity, and reducing the flow path length. Both factors act to reduce the work performed in shearing the fluid, and thereby lead to reduced backpressure.

For example, going from a single tube to two parallel tubes doubles the cross-sectional area, thereby halving the fluid velocity, and additionally, halves the fluid path length. Since backpressure is proportional to length and velocity (and inversely proportional to cross-sectional area), then the backpressure of the two parallel tubing configuration will be ¼ that of the single tube configuration.

A tubing percentage overlap refers to areas where the patient's skin is covered by two layers of tubing. This is described in detail with respect to FIG. 2.

A tubing % patient uncovered refers to area within the wearable heat exchange device 110 where the patient's skin is not covered by heat exchange tubing. For a given size of tubing, this percentage is a function of the size of the stitches, with larger stitches (loops) leading to larger uncovered areas.

An area of heat exchange, is calculated by taking the desired wearable heat exchange device 110 area and subtracting the percentage area where the patient's skin is uncovered by heat exchange tubing A tubing length, provides a metric of how much tubing is used for making a cooling wearable heat exchange device 110. This is calculated by considering the area of heat exchange and overlapped tubing.

A volume of tubing is desirable to be kept small to avoid risks when a cooling/heating wearable heat exchange device 110 is to be used on the same console (e.g. Thermogard XP™) which provides intravascular temperature management (IV™). Thermogard XP™ users are currently instructed to use a 500 mL heat exchange fluid bag (normal saline), which constitutes the largest volume which could be infused into the patient in the event of a catheter leak. A wearable heat exchange device 110 with a large volume would necessitate a larger saline bag (e.g. 1000 mL) which would pose a greater risk to the patient if used for IV™.

A thermal conductivity of (patient) tissue, and depth of major vessel are drivers of heat exchange performance. The major vessel temperature is considered equivalent to the patient's core temperature. This is due to the high convective heat transfer between a major vessel and the major organs of the patient.

A tubing surface temperature, $T_s$, is a temperature of the garment. It is desirable to limit the lower tubing surface temperature as the skin may be injured by extended exposure to excessively cold temperatures (i.e., near-freezing). The console controller may be programmed to limit the lower coolant temperature to a value around 4°-14° C., and additionally may allow the user to select the exact limit. Or the tubing may be chosen to be thick enough to induce a sensible temperature gradient across the tubing wall thickness. In other words, as body heat is transferred from the patient to the tubing, the thermal resistance of the tubing causes the outer surface to warm up compared to the inner surface which is cooled by cooling fluid. In certain embodiments, the console controller may be programmed to limit the lower coolant temperature to around 0°-4° C. In certain embodiments, the lower coolant limit may be held at 0.5° C., since this is the same limit used for IV™, so that a single console could be used for both IV™ and surface cooling without changing the programming or settings. Additionally, this would allow concurrent use of surface and IV™ without reducing the heat transfer of the IV™ by raising the lower coolant temperature limit to a higher value (e.g. 6° C.) than would be needed if using IV™ alone (e.g. 0.5° C.).

To, outflow temperature, (from the heat exchange device 110) is calculated by considering the inflow temperature (to the heat exchange device 110), the flow rate, and the power transferred into the fluid by the patient. This is useful for determining whether the coolant has excess capacity for cooling. For example, an outflow (outlet) temperature of 6° C. indicates that, if the heat exchange device 110 heat exchange area could be increased, additional heat exchange would be possible, because 6° C. represents a large delta from the patient core temperature of 38 C. It also is an indicator of sensitivity of heat exchange to fluid flow rate. For example, if the flow was dropped from 240 mL/min to 120 mL/min, and the inlet was kept at 4° C., then the outlet temp would rise from 6° C. to 8° C. ($d_T$=P/(cp*Q*$\rho$)), where cp is the specific heat capacity, Q is the volumetric flow rate, and $\rho$ is the density of the fluid). The average fluid temperature within the wearable heat exchange device 110 would raise from (6+4)/2=5° C. to (8+4)/2=6° C., which is a difference of 1° C., which is ~a 3% reduction in the available delta from the patient's core at 38° C. and would cause a ~3% reduction in heat transfer.

Viscosity is an input to calculating p, backpressure, generated by pumping fluid through the heat exchange tubing. The backpressure should not exceed the capability of the pump or any of the tubing or components in the fluid circuit. Additionally, it may be desirable to be able to connect an IV™ catheter 119 and a cooling wearable heat exchange device 110 simultaneously. This would afford additional heat exchange to the patient beyond the capabilities of a single device. These two heat exchange devices may be connected in series. Alternatively, they may be connected in parallel. Parallel connections may reduce the heat exchange efficiency of the catheter 119 (due to its high flow resistance), compared to series connections. Additionally, parallel connections may require construction and management of upstream and downstream manifolds. If the devices are connected in series, it is desirable to keep the backpressure of the wearable heat exchange device 110 to a minimum since the IV™ catheter 119 generates backpressure during operation, and any additional backpressure generated by the wearable heat exchange device 110 may place additive stress on all the other components in the flow stream.

Figure 1D:
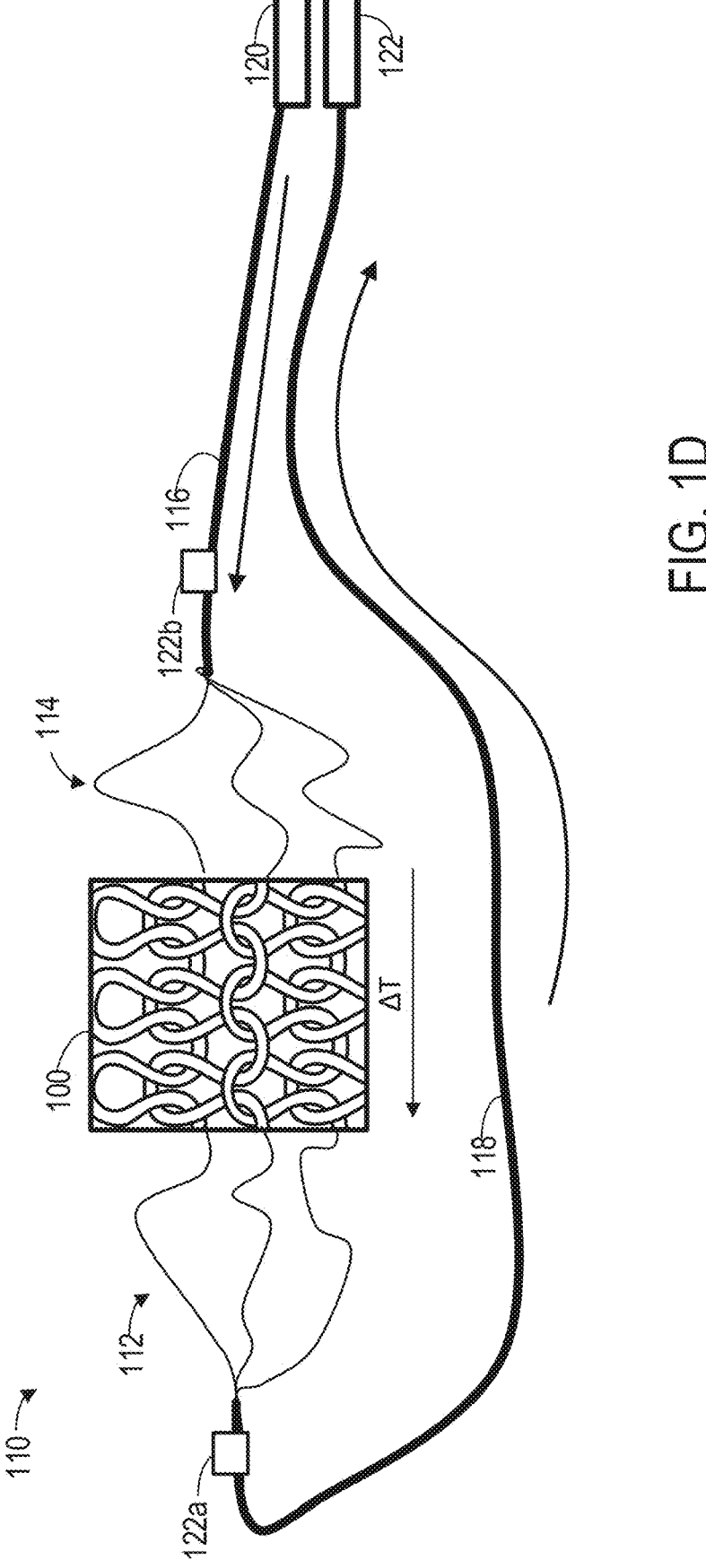
FIG. 1D shows an example of a heat exchange device including the material of FIG. 1A.

FIG. 1D shows an example of a wearable heat exchange device 110 including the material 100 of FIG. 1A. The wearable heat exchange device 110 is configured to work with a temperature management system, such as the heat exchange system 150 of FIG. 1E. The wearable heat exchange device 110 is configured to work with any of the tubing structure patterns of the materials described herein. The wearable heat exchange device 110 can be a consumable device that is connectable to a heat exchange console (e.g., of FIG. 1E). The wearable heat exchange device 110 can form a fluid loop including the material 100. For example, an input line 116 is connected to an input connector 120. The connector 120 is configured to interface with a line extending from a heat exchange console, such as to a damper tube or a pump tube of the fluid loop. Fluid or gas can be pumped through the input line 116 to one of more tube inputs 114 of the material 100.

The tube inputs 114 interface the input line 116 with one or more tubes 102 of the material 100. In some implementations, the tube inputs 114 enable a parallel flow of fluid or gas through each of a plurality of tubes 102. For example, the tube inputs 114 can each be connected to one or more corresponding tubes 102. Where a single tube is used to form the material 100, a single tube input 114 may be used.

The tube outputs 112 interface the output line 118 with the one or more tubes 102 of the material 100. In some implementations, the tube outputs 112 enable a parallel flow of fluid or gas through each of a plurality of tubes 102. For example, the tube outputs 112 can each be connected to one or more corresponding tubes 102. Where a single tube is used to form the material 100, a single tube output 112 may be used. The fluid or gas is pumped through the output line 118 to an output connector 122 configured to connect to the heat exchange console or for gas exchange as applicable.

The fluid loop includes the material 100. A temperature difference ΔT occurs across the material 100 as heat is transferred to or from the patient. Here, a function of the change in temperature ΔT can represent a heating or cooling power applied to the patient by the heat exchange system. The value of ΔT can be measured by temperature sensors 122a-b placed respectively on the input line 116 and output line 118.

The wearable heat exchange device 110 can be used for different patient types. For example, the size of the material 100 can be adjusted based on the patient. The wearable heat exchange device 110 can be sized and used for neonatal patients. The wearable heat exchange device 110 can be sized and used with pediatric patients. The wearable heat exchange device 110 can be sized and used with adult patients. The wearable heat exchange device 110 can be reusable or be disposable.

The wearable heat exchange device 110 is configured for low backpressure, high pressure, and low volume (e.g., low flow) from the pump of the heat exchange system. The one or more tubes of the material 100 have a relatively low internal volume compared to a balloon or conventional heat exchange pad. For example, the wearable heat exchange device 110 is compatible with a conventional 500 mL saline bag. The size of the knit pattern loops can be changed to allow access to the patient skin under the wearable heat exchange device 110. For example, the wearable heat exchange device 110 can include a space in the knit pattern to allow access of an intravenous catheter to the patient's body. The wearable heat exchange device 110 is form fitting and hugs the body of the patient, improving heat exchange efficiency as subsequently described.

Figure 1E:
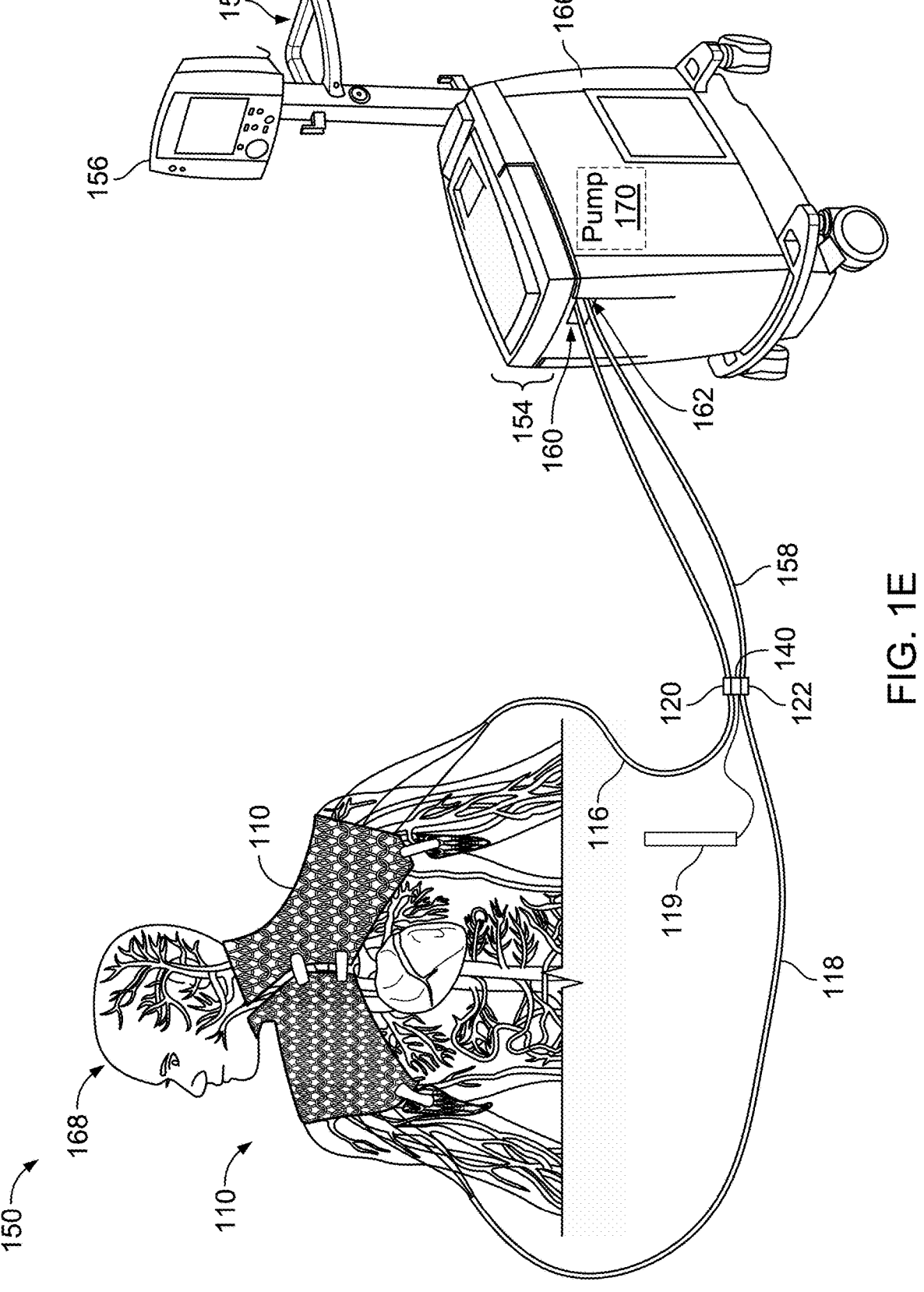
FIG. 1E shows an example of a temperature management system including the heat exchange material of FIG. 1A in the heat exchange device of FIG. 1B.

FIG. 1E shows an example of a temperature management system 150 including the material of FIG. 1A forming a heat exchange device e.g., a wearable heat exchange device for applying to the surface of a patient 110. The temperature management system 150 is configured to control a temperature of a patient 168 body using the heat exchange device 110 described herein. The temperature management system 150 is configured to heat or cool the patient (or both) to manage the temperature of the patient. Managing the temperature of the patient may be referred to as heat exchange treatment of the patient, or heating/warming or cooling treatment of the patient. The temperature management system 150 includes a conformable wearable heat exchange device 110 made of the material 100, which may be applied to the surface of a patient 168. The temperature management system 150 can include other hardware configured for heating or cooling the patient, such as heat exchange fluid loops, heating or cooling plates, heating or cooling cassettes, heat exchange baths, and so forth as subsequently described for heating or cooling the patient (or both).

The temperature management system 150 includes an extracorporeal control console with a hardware interface 154, subsequently described. The interface 154 allows the heat exchange device 110 to be coupled to the control console 152 by interfacing with a heat exchange fluid loop that includes the heat exchange device and a tubing assembly. The control console 152 includes a controller and/or processor for controlling a heating and cooling for the heat exchange device 110. The control console 152 includes a user interface 156 for allowing a user to input data or control signals to the temperature management system 150 and to present information, such as treatment data, indicative of treatment of the patient using the temperature management system 150. In some implementations, the control console includes a control console of the Thermogard XP® (TGXP) Temperature Management System, commercially available from ZOLL Circulation Inc. in San Jose, California. In some implementations, the control console includes a control console of the temperature management system as described in U.S. patent application Ser. No. 17/561,512, titled Improved Temperature Management Systems and Methods for Ease and Timing of Setup and Operation and filed Dec. 23, 2021, U.S. Pat. No. 11,185,440, titled Devices, Systems and Methods for Endovascular Temperature Control and filed Feb. 2, 2017, U.S. Pat. No. 11,116,657, filed May 12, 2017 and titled Devices, Systems and Methods for Endovascular Temperature Control, and U.S. Pub. No. US20190133820, titled Devices, Systems and Methods for Endovascular Temperature Control, filed Aug. 1, 2018, each of which is incorporated herein in entirety by reference.

The temperature management system 150 is configured to measure operational data representing operation of one or more hardware aspects of the temperature management system 150 and patient data. The operational data and the patient data that are measured during treatment of the patient may be referred to as treatment data. The temperature management system 150 is configured to measure patient data representing one or more physiological parameters of the patient, e.g., patient temperature, during treatment of the patient. The temperature management system is configured to control the temperature of the patient's body based on the operational data (e.g., pump speed, coolant temperature, and power), and/or patient data, (e.g., patient temperature feedback received from temperature sensors located in or on the patient). The temperature management system 150 is configured to display, by a user interface, an operational status of the temperature management system 150 and a physiological status of the patient during treatment.

The operational status can include whether the temperature management system 150 is working at a maximum cooling or heating power output (e.g., effort) or a percentage of the maximum heating or cooling power output. The heating or cooling power output is proportional to the heating or cooling rate of the patient 168. The heat exchange device 110 enables the heat exchange system 150 to maximize the maximum possible heat exchange rate and increase an overall heat exchange rate for a given heating or cooling power output. The efficiency of the heat exchange device 110 is increased by forming the heat exchange device 110 to conform to target regions of the patient. The efficiency of the heat exchange device 110 is increased by forming the heat exchange device 110 to eliminate overlapping material on the heat exchange device 110. The efficiency of the heat exchange device 110 is increased by forming the heat exchange device 110 to conform to contours of the patient 168.

A power value representing the cooling or warming power delivered by the temperature management system 150 to cool or heat the patient is displayed on the user interface 156. The cooling or warming power (also called "effort" or simply "power") represents how hard the temperature management system 150 is working to raise, lower or maintain the patient's temperature, e.g., by cooling or warming. The actual value of the power represents a percentage or fraction of a maximum possible cooling or warming power capability of the system to cool or warm the patient based on a relationship between a working fluid, saline, bath or coolant temperature of the temperature management system 150 and the patient's current temperature.

One or more temperature sensors 122a, 122b may be located on or in the heat exchange device 110, and/or may be located on a separate device or probe positioned elsewhere in the body. In some implementations, the heat exchange device 110 and tubing assembly 158 of the fluid loop and/or the temperature sensors 120a-b may be disposable items intended for a single use, while the control console 154 may be a non-disposable device intended for multiple uses.

The extracorporeal control console 152 generally comprises a main housing and a console head having a user interface 156. The main housing 166 includes various apparatuses and circuitry for warming/cooling thermal exchange fluid, e.g., coolant, refrigerant, saline, to controlled temperature(s) and for pumping such warmed or cooled thermal exchange fluid through the heat exchange device 110 to effectively modify and/or control the subject's body temperature. On the housing 166, there are provided connection ports 160, 162 for connection of additional or alternative types of temperature sensors and/or other apparatuses. Connectors 120, 122 can connect the tubing of the tubing assembly 158 from the console 152 to the inflow tube 116 and outflow tube 118 of the heat exchange device 110.

In certain implementations, the heat exchange device 110 may be encoded with or may be coupled to a sensing module 140 that is encoded with device identifying information that transmits a signal to or is read by the console processor, and causes the processor to use algorithms and/or operational settings/variables that are specific to the particular heat exchange device 110, e.g., a garment type, a heat exchange device size or shape, a knit pattern of the heat exchange material 100, heating and cooling properties of the heat exchange device 110, tube size of the heat exchange material, or other properties of the heat exchange device or heat exchange material.

The encoded information may include, or cause the console processor to select and use algorithms and/or operational settings or data that are suitable for any available heat exchange device 110 of a set of heat exchange devices for calibration of the heat exchange system 150. Specifically, the encoded information may include the particular algorithms and/or operational settings or data to be used, or alternatively the console processor may be pre-programmed with a number of different algorithms and/or operational settings or data and may be further programmed to select and implement, on the basis of the encoded data, the algorithm and/or operational settings or data suitable for the heat exchange devices that are useable or approved for use with tubing assembly and/or the console 152. For example, in certain embodiments, each of the plurality of approved heat exchange devices 110, may have a recommended pressure limit and the encoded information may include, or cause the processor to select and use, a control algorithm, operational setting or data that limits the speed of a pump 170 such that heat exchange fluid pressure within the heat exchange device 110 connected to the tubing assembly 158 will not exceed a maximum pressure limit for that heat exchange device, irrespective of which of the plurality of heat exchange device types is connected to the tubing assembly 158.

The temperature management system 150 is configured to control the body temperature of the patient, as previously described. The processor (e.g., a system controller) of the console of the temperature management system 150 receives values of one or more patient data and/or operational data from one or more sensors of the temperature management system 150 as the patient's body temperature is changed by the heat exchange device.

The one or more sensors for measuring patient data may include a temperature sensor, e.g., a thermistor or thermocouple or temperature probe, positioned on or in the patient. The one or more sensors for measuring the operational data of the temperature management system 150 can vary depending on the hardware configuration of the temperature management system 150 and depending on the operational data being measured. For example, the sensors can include one or more temperature sensors (e.g., thermistors), a fluid flow rate sensor or flow meter, a pressure sensor, e.g., pressure transducer or monometer, an ammeter or other sensor for measuring power consumed by one or more components of the temperature management system 150, a tachometer or other sensor for measuring pump rotations per minute (RPM) or pump impeller speed, and so forth for measuring the values of the operational data. Some operational data can be determined indirectly, such as determining cooling energy or power delivered by the heat exchange device by measuring patient and heat exchange bath temperatures using temperature sensors, or by measuring a change in working fluid temperature $T_{in}$–$T_{out}$ (where $T_{in}$ is the temperature of working fluid flowing into a heat exchange device and $T_{out}$ is the temperature of the working fluid flowing out of the heat exchange device) during operation of the temperature management system 150 via temperature sensors located in the catheter inflow and outflow lumens or in inflow and outflow lumens of the tubing assembly.

The temperature management system may include a processor, a memory, and associated circuitry coupled to the one or more sensors for detecting operational or patient data. The operational and patient data are collected and/or stored in the system for retrospective, current or other review. For example, the operational and patient data can be stored as log entries. In certain implementations, the log entries can each be structured messages that include particular values associated with the heat exchange treatment, generated from data messages. For example, the data messages can indicate a current snapshot of the operation of the temperature management system 150. In this case, the values of the data message include a list of operational values (and in some implementations, patient temperature data). The operational values can be parsed from the data messages (e.g., by a remote device) and used to populate a screen or display of a remote computing system. For example, the temperature management system 150 can transmit a stream of data including the data messages to a remote system for remote monitoring of the operation of the temperature management system 150. In some implementations, the processor is configured to stream digital output data having the patient temperature data and the operational data to a remote server. In some implementations, operational and patient data may be transmitted or streamed in real time or near real time via a wired, RS-232 streaming output on the system console to a remote processor or computer, e.g., to an EMR data hub or hospital hub. In some implementations, operational and patient data may be transmitted or streamed in real time or near real time over a WiFi communications, Bluetooth, cellular, USB or other wireless connection or link.

The temperature management system 150 can generate one or more alerts to indicate a status of the patient, a status of one or more components of the temperature management system 150, or a combination thereof. The alerts can be generated based on the treatment log data or data of the data messages. The alert can be generated for presentation on a user interface of the temperature management system 150. The processor may send the alert to one or more other computing devices, such as computing devices associated with a health care provider of the patient. In an aspect, the user interface 154 is configured to communicate with the processor, wherein the data representing the alert indicating whether a fault has occurred, a stage of treatment has initiated/completed, or any other relevant aspect of the treatment of the patient that satisfies a notification rule causes a notification to be displayed on a user interface. The user interface may be coupled to the console via a wire or wirelessly (e.g., the user interface may be a portable tablet or remote computing device).

Figure 2:
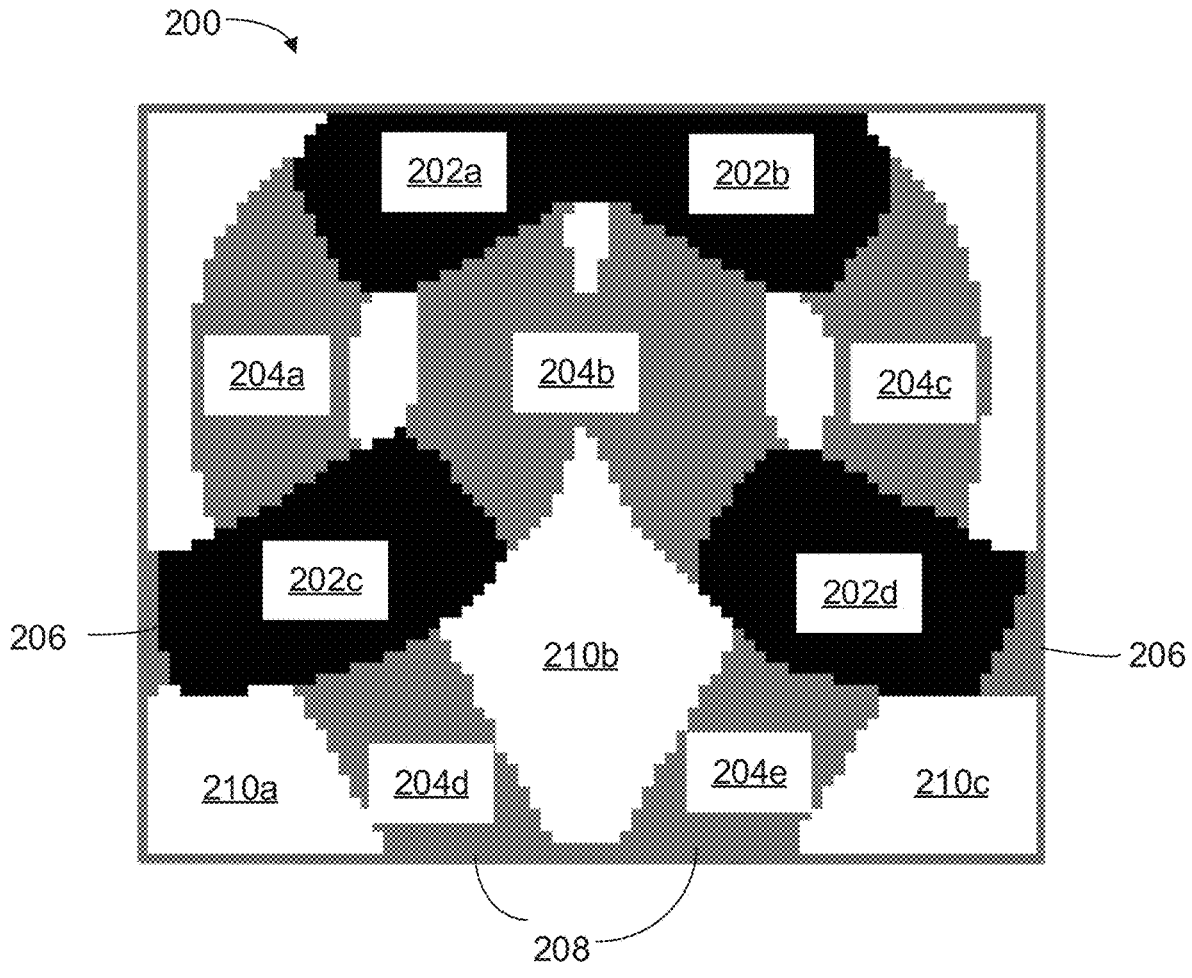
FIG. 2 shows an example of a tubing pattern including areas of overlap.

FIG. 2 shows an example of a tubing pattern 200 including areas of overlap. The tubing pattern 200 shown in FIG. 2 may include two portions of a single tube (a first portion 206 and a second portion 208) or two separate tubes (a first tube 206 and a second tube 208). The first portion or first tube 206 overlaps with the second portion or second tube 208 in the regions 202a, 202b, 202c, and 202d. There is no tubing covering the patient's skin at regions 210a, 210b, or 210c for a single layer of the heat exchange material having the pattern 200. Exactly one of portion or tubes 206, 208 is exposed to the skin of the patient at regions 204a, 204b, 204c, 204d, and 204e. In some implementations, the regions 210a-c of no tubing coverage is less than 35% of the overall area covered by the heat exchange material 100. In some implementations, the overlapping regions include between 20%-35% of the overall area covered by the material 100. In some implementations, the areas 204a-e of exactly one tube coverage includes about 30-80% of the overall area covered by the material 100. The material 100 has a high volumetric efficiency because the diameter of the tubing is less than the typical thickness of the water channels in a conventional heat exchange pads. For example, conventional heat exchange pads include larger fluid channels to allow flat pads to be bent around three-dimensional patient anatomy. Bending pads typically results in deformation or creasing of the pads, which would interfere with liquid flow if the channels were too thin. Additionally, conventional pads can require larger extension tubing connecting the pad to a console or system. The material 110 uses a relatively low volume of heat exchange fluid compared to conventional pads to result in a high rate of heat exchange or gas for gas exchange. The material 110 may include smaller tubing and smaller extension tubing connecting the material to a temperature management system because it requires a lower volume of fluid and lower flow rate to achieve optimal heat exchange with a targeted region of the patient's body.

Figures 3A, 3B:
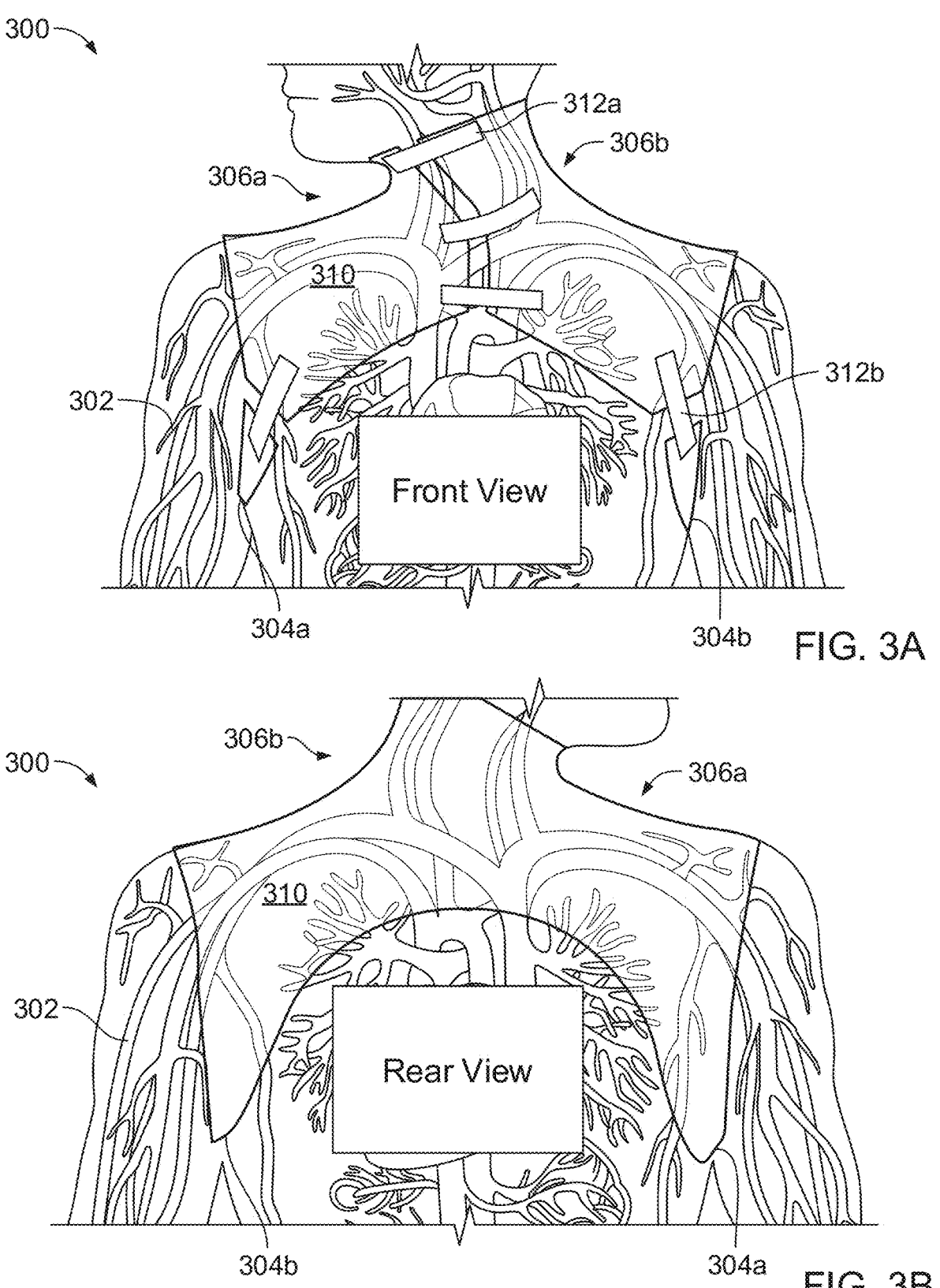
FIGS. 3A-3B each show an example of a heat exchange device over a vasculature of a patient.

FIGS. 3A-3B each show a view of an example heat exchange device 300, e.g., wearable heat exchange device, over a vasculature 302 of a patient. The heat exchange device 300 includes a heat exchange material 310 (e.g., material 100 of FIGS. 1A-1C). The heat exchange device 300 is shaped to conform to a neck areas 306a-b of the patient. The heat exchange device 300 is configured to form to areas 304a-b under the arms of the patient. The heat exchange device 300 fits snugly on the patient and conforms to contours of the patient's body.

The heat exchange device 300 is shaped to target areas 304, 306 of the patient's body in which the vasculature 302 is dense, close to the skin surface, or both. The skin of the patient resists the thermal exchange of the heat exchange device with the patient's vasculature. To increase the heating and cooling efficiency of the heat exchange device 300, and maximize the heating or cooling rate that the heat exchange device can deliver, areas with minimal thermal resistance are targeted. The size of the heat exchange device 300 can be reduced to fit the particular patient. The size of the heat exchange device 300 can be reduced to target the specific areas of interest. The heat exchange device 300 heats and cools only the areas 304, 306 of the patient in which thermal exchange is most efficient. This enables a high pressure, low volume heat exchange device 300 to be used in which less fluid is needed to heat or cool the patient. This enables the heat exchange device 300 to be used with existing catheter-based temperature management systems that require low volume and high pressure. For example, the heat exchange device 300 can use a same fluid source, tubing, and control console as other low volume heat exchange systems, such as catheter-based systems, e.g., ZOLL's Thermogard XP temperature management system. This can reduce a risk of user error and enable concurrent use of the heat exchange device 300 with low volume heat exchange devices such as catheters. The overall volume of the tubes is reduced in comparison to the volume of a non-targeted heat exchange device or in comparison to traditionally constructed surface pads.

The conformability allows the heat exchange device 300 to conform to contours of the patient. The heat exchange device 300 can be shaped to fit the patient. The heat exchange device 300 wraps around the back of the patient without folds or wrinkles in the heat exchange material 310. The reduced folds or wrinkles eliminate or reduce areas of the heat exchange device 300 in which the heat exchange device is not contacting the patient's skin. Additionally, the lack of folds or wrinkles allows a low fluid volume device to be constructed without risking occlusion or significant constriction of the fluid passage (lumen). The heating and cooling efficiency of the heat exchange device 300 can be increased relative to the heat exchange efficiency of heat exchange devices having non-contacting areas from wrinkles or folds. The heat exchange device 300 can move and contort to match movement of the patient without losing contact of the patient.

An increased heating or cooling rate for the patient enables finer control of the heating and cooling treatment of the patient. The heat exchange system 150 had heat or cool the patient more precisely using the higher heat exchange rate. The conformable heat exchange garment may be effectively applied to areas of higher heat flux on the patient than what was previously allowed by traditional pads. A high heat flux reduces thermal lag and overshoot of the patient temperature for temperature control. For example, the garment may be applied to the neck region to provide a localized cooling effect on the brain. A benefit of cooling the neck region is high heat flux due to the proximity of major blood vessels to the skin. Major vessels of the vasculature 302 are relatively superficial and accessible in the head, neck, clavicle, and axilla regions included in regions 304, 306 and covered by heat exchange material 310. There is a short conduction path to the core body temperature of the patient, resulting in an increased heat flux (relative to other regions) and further reducing lag in thermal control. The axilla regions 304 have a 2-1 surface contact ratio and offer an anchor point.

The shape and size of the heat exchange device 300 enables a simple application of the device 300 to the patient. The heat exchange device 300 does not require adhesive to conform to the patient because the heat exchange device is already shaped, by the knit pattern of the heat exchange material 100, to conform to the patient. The heat exchange device 300 may be a unitary piece. In certain implementations, fasteners 312*a* near the neck regions 306 and fasteners 312*b* near the axilla regions 304 may be used to secure the heat exchange device 300 onto the patient. Fasteners 312*a*-*b* can include Velcro straps, clasps, hooks, buttons, zipper or any similar fastener.

Figures 3C, 3D:
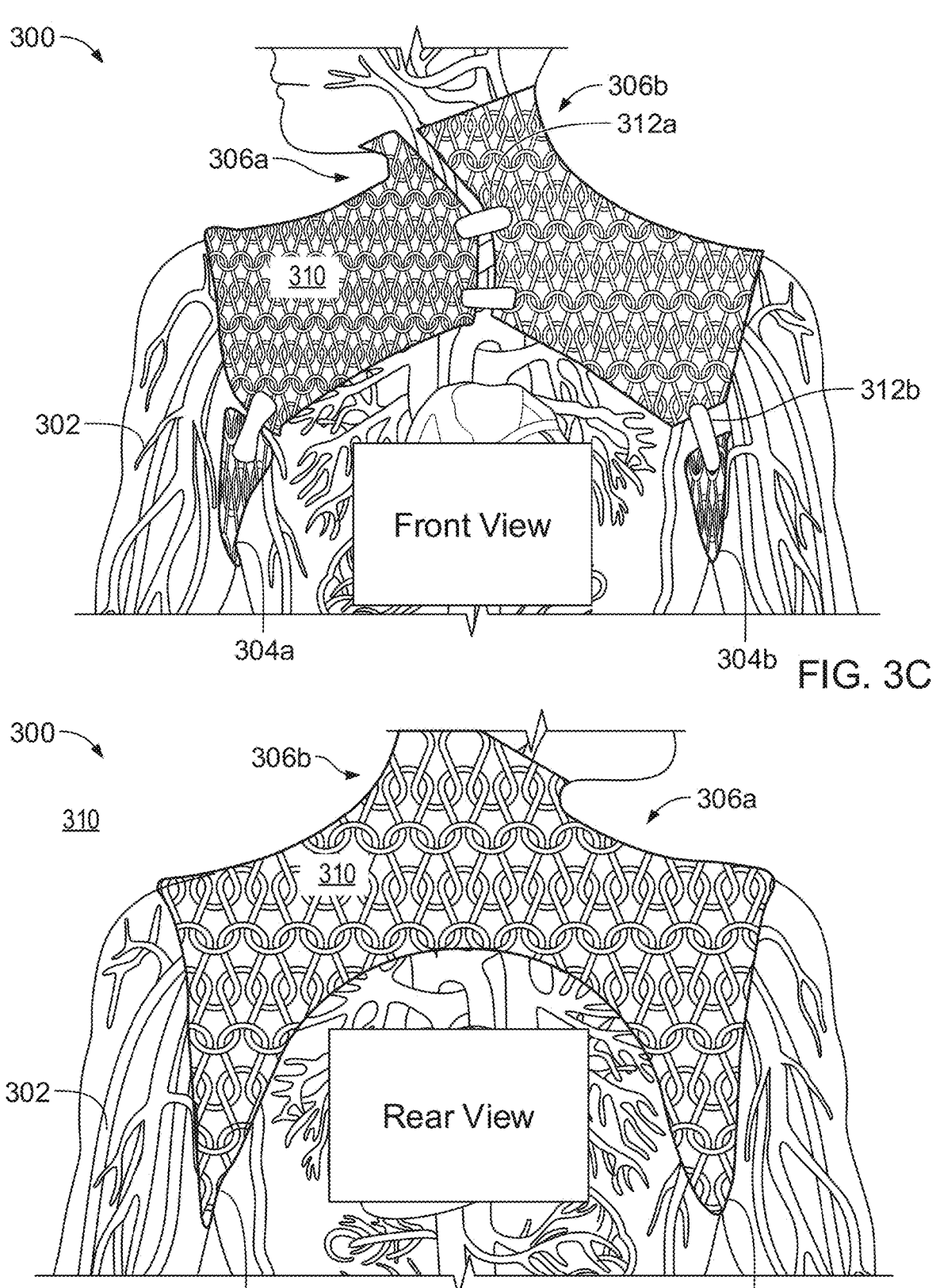
FIGS. 3C-3D each show an example of a heat exchange device over a vasculature of a patient.

FIGS. 3C-3D each show an example of a heat exchange device 300 e.g., wearable heat exchange device, over a vasculature 302 of a patient. The heat exchange device 300 includes the knit pattern described in relation to FIGS. 1A-1E. The heat exchange device 300 covers the clavicle and neck regions 306*a*-*b* of the patient and the axilla regions 304*a*-*b* of the patient. The heat exchange device 300 is a single piece of knitted material that wraps around and under the armpits of the patient near regions 304*a*-*b*, contacting the arms and torso of the patient for heat exchange. The heat exchange device 300 is shaped to hug the neck of the patient.

Figure 3E:
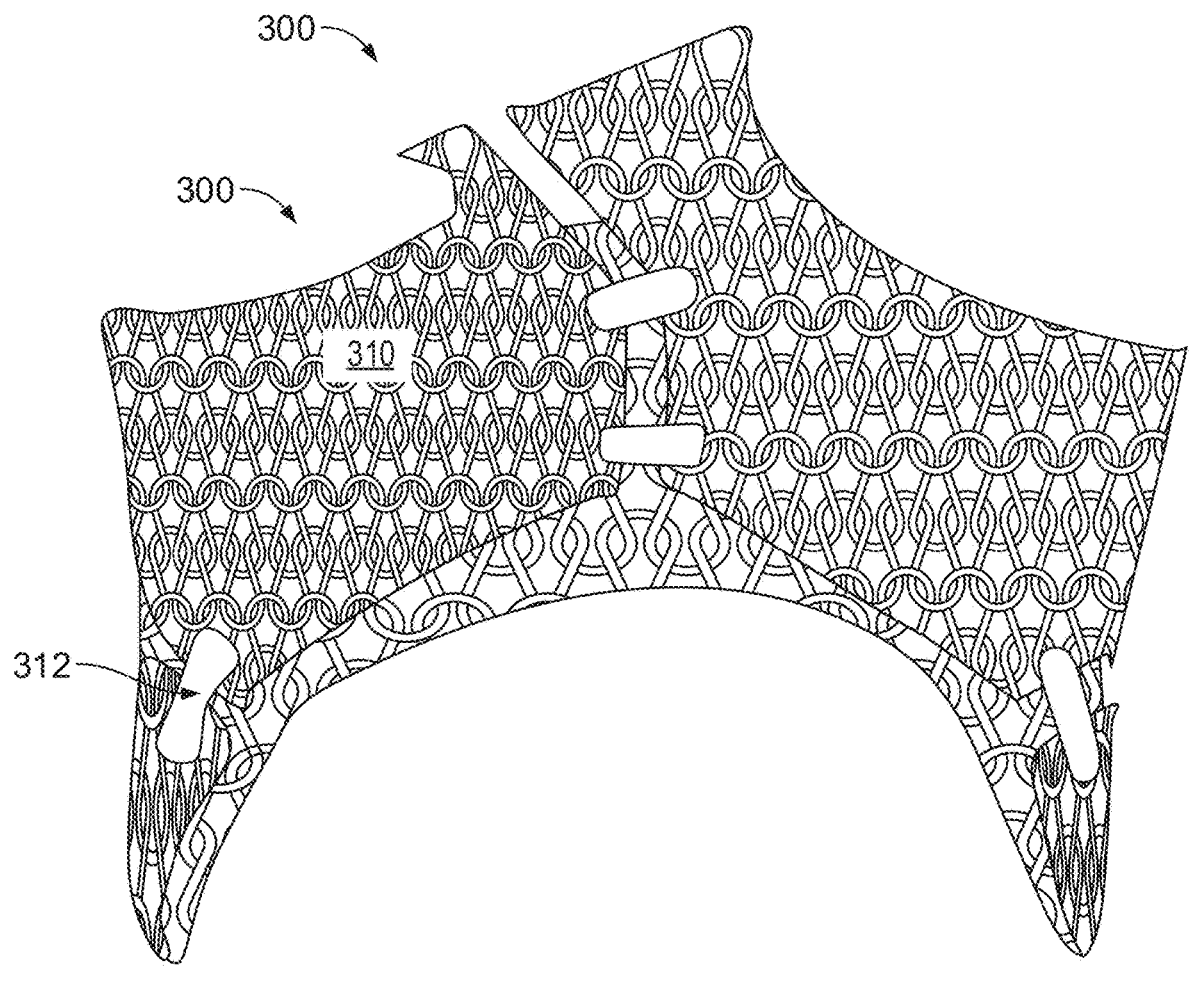
FIG. 3E shows an example heat exchange device.

FIG. 3E shows an example of the heat exchange device 300 e.g., wearable heat exchange device, in space. The heat exchange device 300 may be a unitary piece, or may connect with a plurality of fasteners 312 and does not require adhesive or folds to secure the device to the patient. The one or more tubes of the heat exchange material 310 are configured to bend without crimping or preventing fluid or gas to flow in the one or more tubes due to the wall thickness and interior diameter of the one or more tubes, as previously described. The heat exchange material 310 is shaped to fit around the armpits of the patient. The heat exchange material 310 can be folded or contorted without pinching the one or more tubes of the heat exchange material because of the flexibility provided by the tube interconnection between tubes or the interconnection between portions of a single tube. Even if the heat exchange material 310 is folded, the one or more tubes are not crimped due to the thickness of the tube walls.

Figure 4:
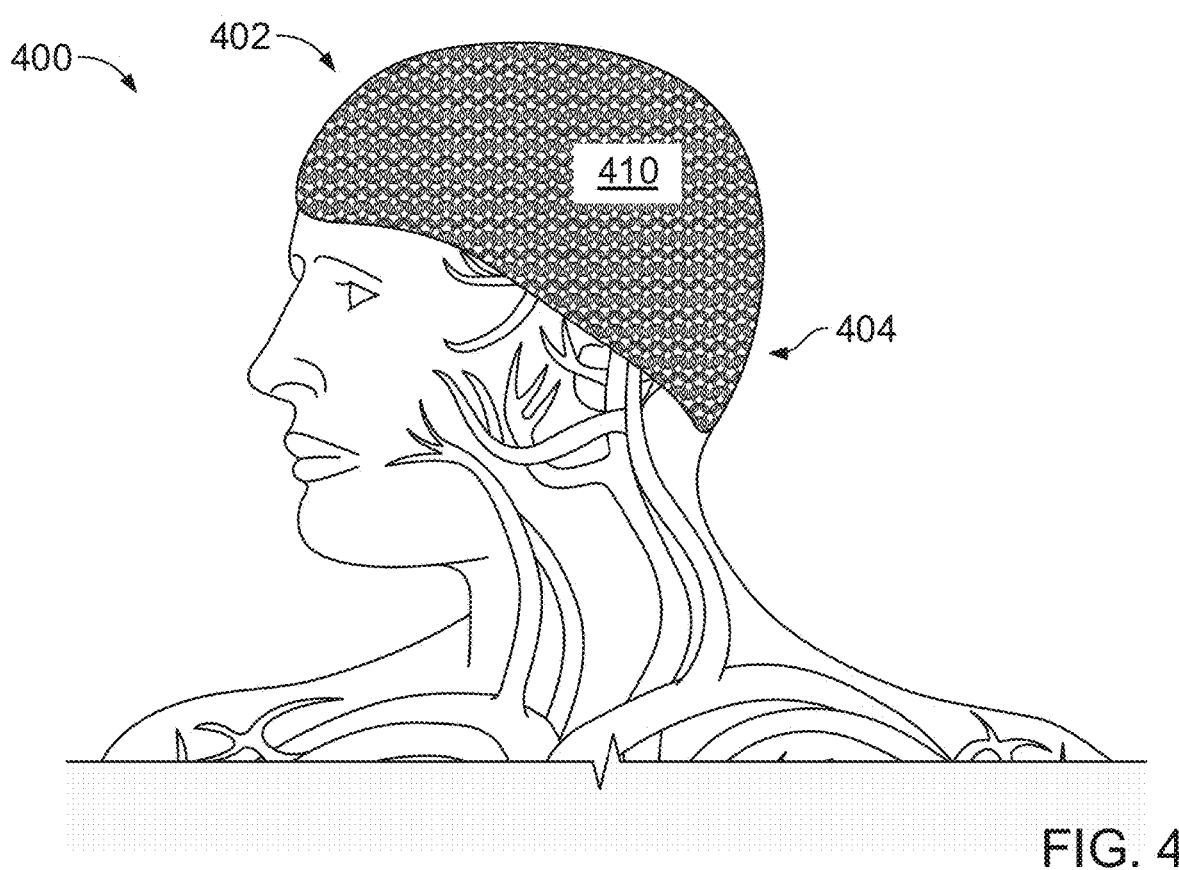
FIG. 4 shows an example heat exchange device for a head of a patient.

FIG. 4 shows an example heat exchange device 400 for a head of a patient. The heat exchange device 400 is configured to follow a contour 402 of the patient's head. The heat exchange material 410 of the heat exchange device 400 does not have folds, gaps, or wrinkles when placed on the head of the patient. The heat exchange device 400 is shaped using the tube interconnection to conform to the curved surface 402. The heat exchange device 400 provides a uniform, snug fit on the head of the patient with constant or nearly constant contact over the entire head of the patient, maximizing a heat transfer rate. The overall volume of the heat exchange device 400 can be reduced to only that needed to heat and cool the desired portions of the user's head. Nearly all of the volume of the tubes of the heat exchange device 400 is in direct contact with the target heat exchange region of the patient. The heat exchange device 400 extends to a neck region 404 of the patient to target the patient's head.

Figure 5:
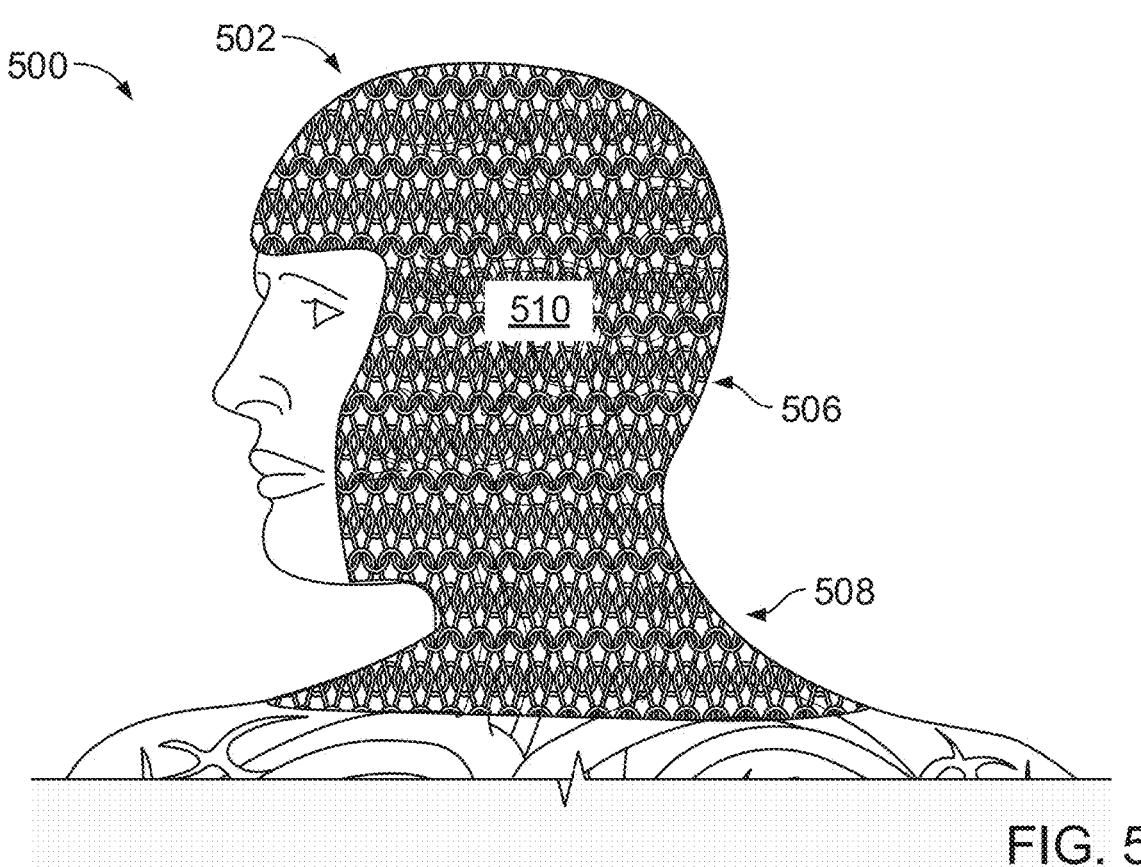
FIG. 5 shows an example heat exchange device for a head of a patient.

FIG. 5 shows an example heat exchange device 500 for a head of a patient. The heat exchange device 500 is configured to follow a contour 502 of the patient's head. The heat exchange device 500 does not have folds or wrinkles when placed on the head of the patient. The heat exchange device 500 extends to the neck region 508 of the patient to create a constant contact with the patient's head 506 and neck region 508 without folds, wrinkles, or gaps in the heat exchange material 510. The heat exchange device 500 is shaped using the tube interconnection to conform to the curved surface 502. The heat exchange device 500 provides a uniform, snug fit on the head of the patient with constant or nearly constant contact over the entire head of the patient, maximizing a heat transfer rate. The heat exchange device 500 can move as the patient's head and neck move, allowing patient mobility during use. The overall volume of the heat exchange device 500 can be reduced to only that needed to heat and cool the desired portions of the user's head 506 and neck 508. Nearly all of the volume of the tubes of the heat exchange device 500 is in direct contact with the target heat exchange region of the patient. In some implementations, the heat exchange device 500 can be integrated with device 300 previously described to have a constant heat exchange layer contacting the patient from the head, down the neck and clavicle, and to the axilla. For example, the heat exchange device 500 can be a single piece of material extending to the axilla of the patient. In some implementations, the heat exchange device 500 can be a separate piece of material that connects to or interlocks with a second heat exchange device 300 that forms a vest as previously described.

Figure 6:
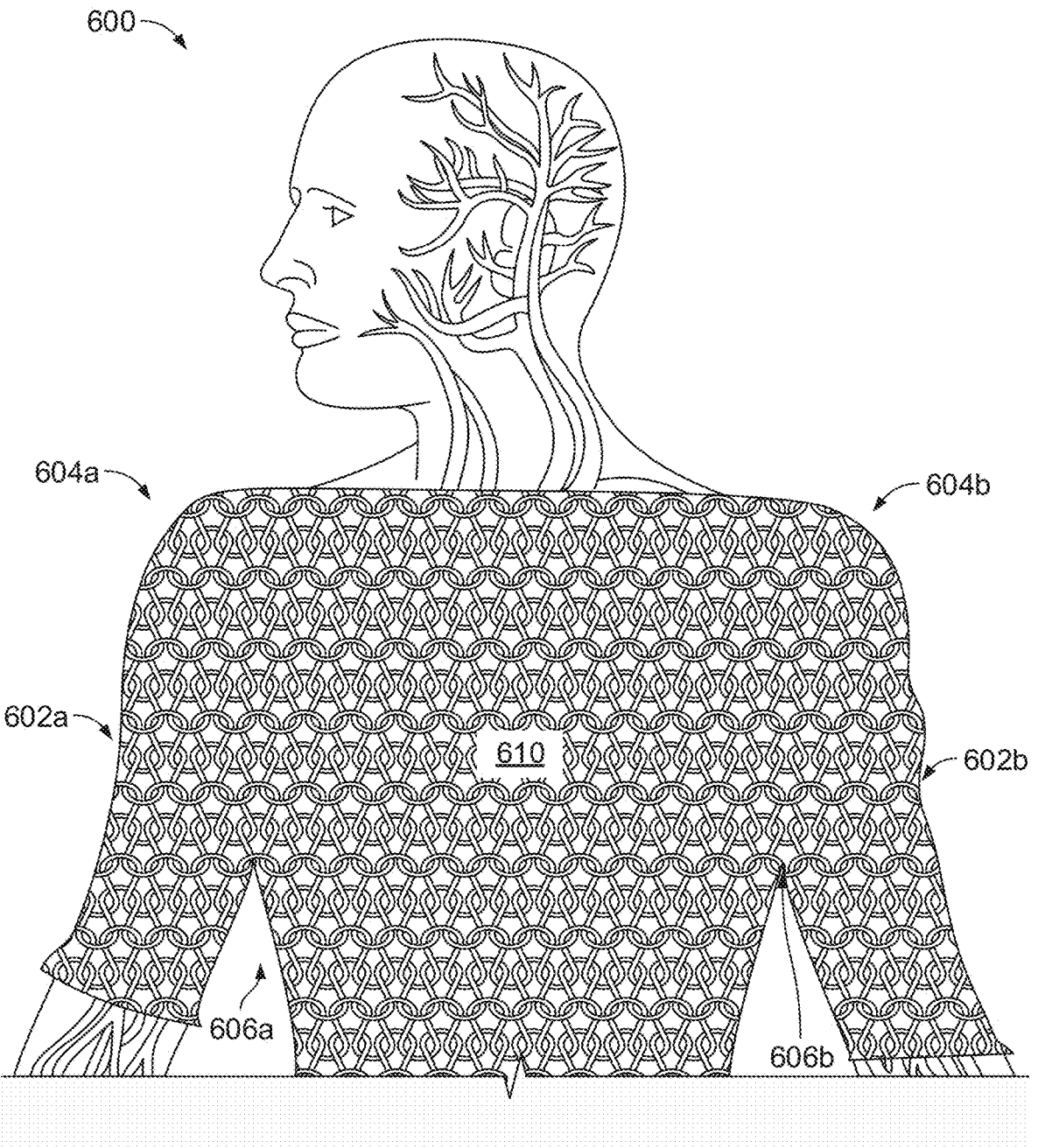
FIG. 6 shows an example heat exchange device for a body of a patient.

FIG. 6 shows an example heat exchange device 600 for a body of a patient. The heat exchange device 600 forms a shirt for covering the entire torso of the patient in a single, monolithic piece of material 610. In this example, the heat exchange material 610 includes a knitted pattern, such as described in relation to FIGS. 1A-1E. The heat exchange device 600 is configured to cover the shoulders 604a-b of the patient. The heat exchange device 600 is configured to cover the axilla 606a-b of the patient. The heat exchange device 600 is configured to cover the arms 602a-b of the patient with sleeves of the heat exchange material 610. The heat exchange material 610 conforms to the patient without substantial wrinkles, gaps, or folds. The heat exchange material 610 therefore has a nearly constant or constant contact with the patient's skin for the entire region covered by the heat exchange device 600. The heat exchange device 600 allows patient movement while still conforming to the patient's skin without gaps or substantial wrinkles. In certain implementations, the heat exchange material may be configured to cover all or a portion of the patient's legs or other body portions below the waist, e.g., forming a wearable pants or shorts.

Figure 7:
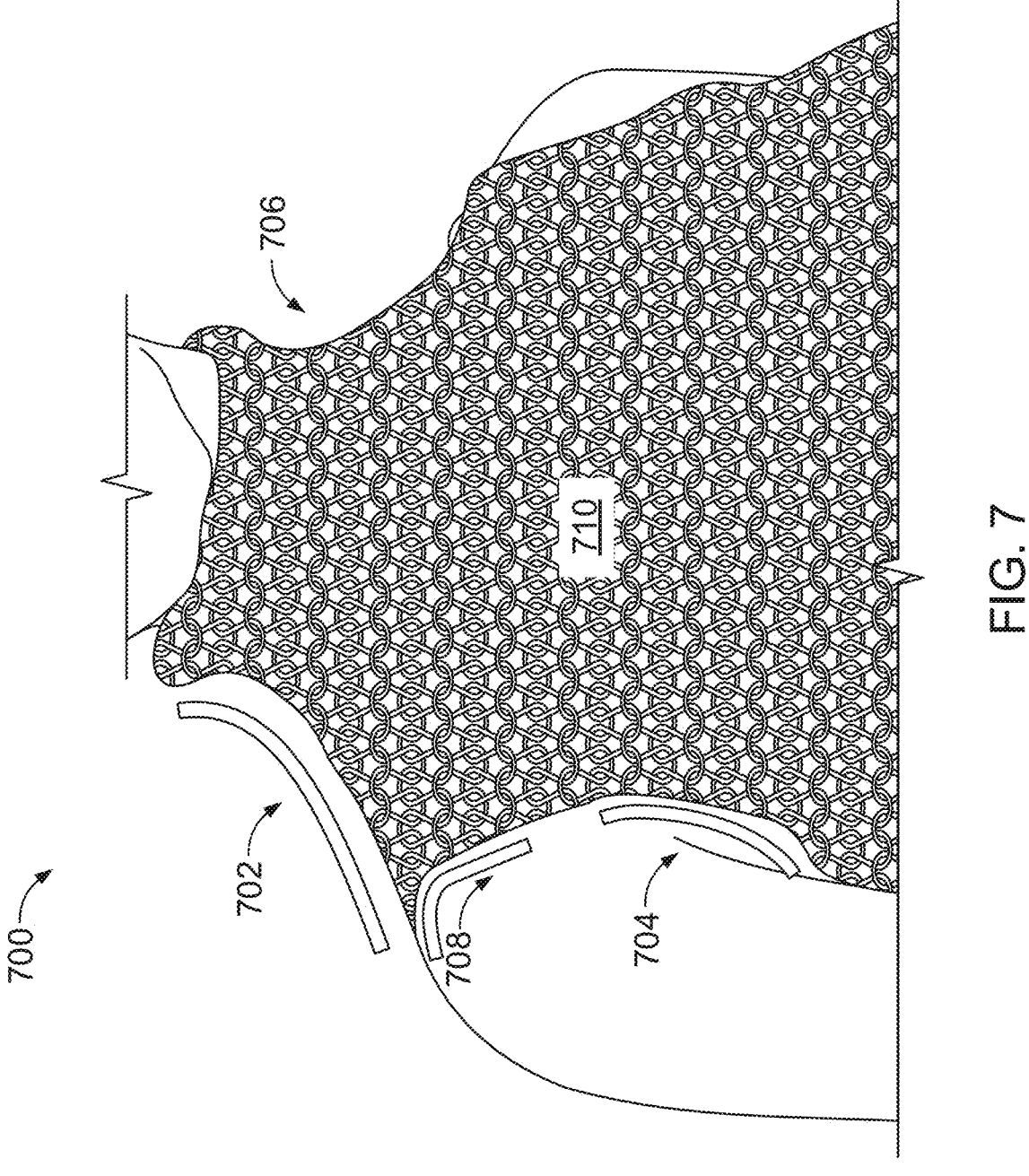
FIG. 7 shows an example heat exchange device for a body of a patient including contours of the heat exchange device.

FIG. 7 shows an example heat exchange device 700 for a body of a patient including contours 702, 704, 708 of the heat exchange device. The heat exchange device 700 is similar to the heat exchange device 600. The heat exchange device 700 has no sleeves. In some implementations, the heat exchange device 700 may be a single unitary piece of material. In some implementations, the heat exchange device 700 includes fasteners such as described herein. The heat exchange device 700 extends up the neck 706 of the patient. The heat exchange device 700 has contours that fit snugly on the patient's body, conforming to any curves of the patient's body without folds, wrinkles, or gaps. The heat exchange device 700 is formed with curves 702, 704 in the material 710 itself to promote the form fit to the patient. The heat exchange material 710 can include the tube interconnection described in relation to FIGS. 1A-1E.

Figure 8:
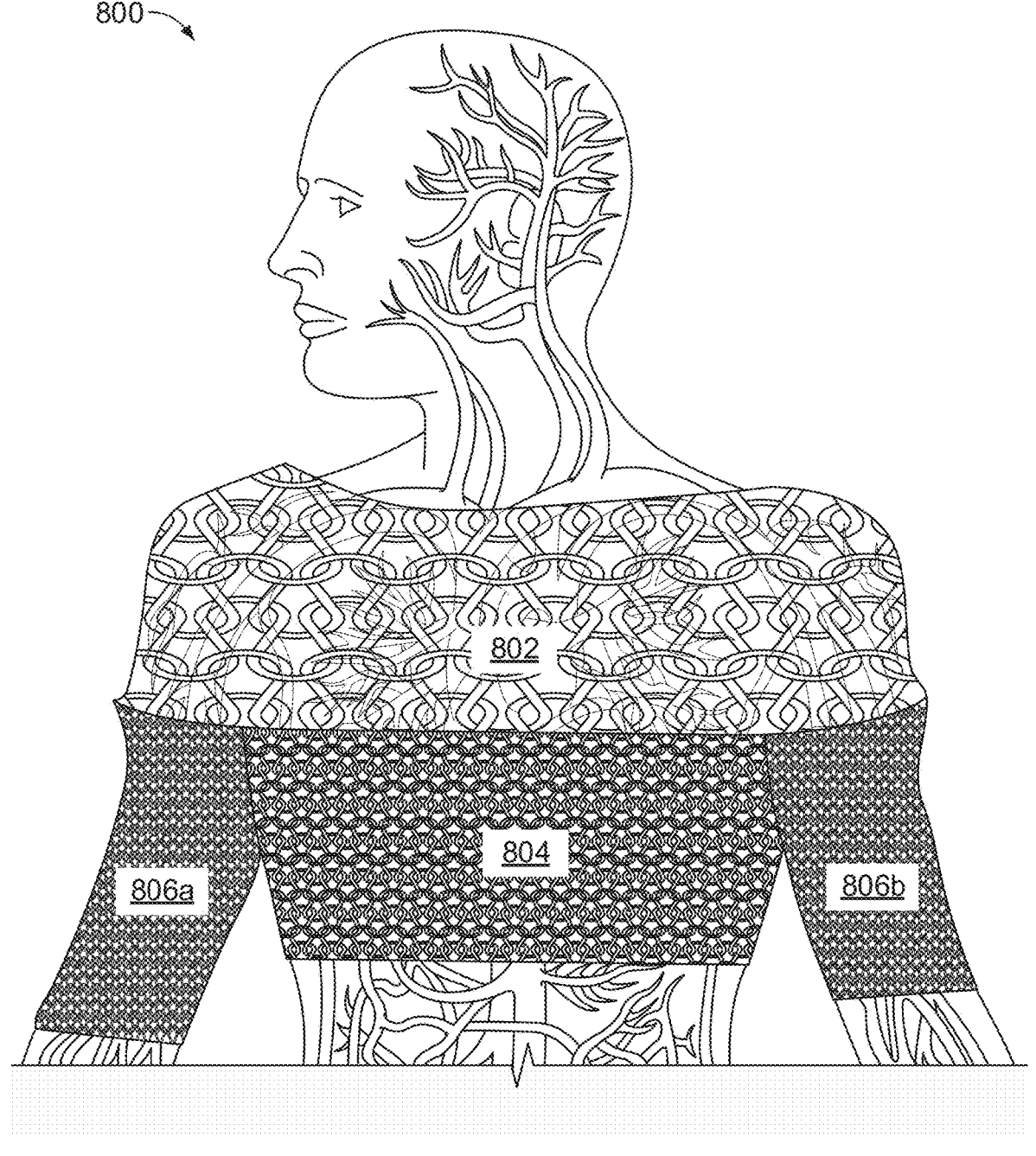
FIG. 8 shows an example heat exchange device including a plurality of tubing interconnection pattern sizes.

FIG. 8 shows an example heat exchange device 800 e.g., a wearable heat exchange device, including a plurality of tubing interconnection pattern sizes. The heat exchange device 800 can be similar to the heat exchange device 600 previously described. The heat exchange device 800 includes variable tube interconnection patterns (e.g., knit patterns, weave patterns, braid patterns, etc.). The heat exchange device 800 includes several different regions, such as a clavicle region 802, a body region 804, and sleeves 806a-b. The regions 802, 804, and 806 are chosen for illustration, but any combination of regions be included. For example, there can be two different regions, three different regions, or any number of different regions. The regions can be located anywhere in the heat exchange device 800 can be sized and shaped as needed. In an example, any of the heat exchange devices described herein may be divided into regions of different tubing patterns as described in relation to heat exchange device 800. For example, heat exchange device 300, 400, 500, 600, and 700 can each be segmented into regions of different tube interconnection patterns.

The different regions 802, 804, 806 each include a different tube interconnection pattern for forming the heat exchange material. For example, the heat exchange device 800 can include several different knit patterns. Each knit pattern can include tube loops of different sizes. For example, sleeves 806a-b may include tube loops with smaller diameters than clavicle portion 802. In some implementations, the opposite configuration is used: the clavicle region 802 has smaller loops than sleeves 806a-b or body 804 regions. Each knit pattern can include tubes having different numbers of interconnected neighbors or a single tube with portions or sections of the tube having different numbers of interconnecting neighbor portions or sections, A knit pattern or the loops having different sizes can result in a non-planar knit pattern or fabric that retains a particular three-dimensional shape.

The regions can be specifically designed for a respective region of the patient. For example, the heat exchange device 800 can include a particular pattern for a higher-mobility region of the patient to allow for needed flexibility or in that area. For example, the neck region may have an interconnection pattern allowing for a relatively flexible heat exchange material to allow neck movement without impediment or blocking fluid flow. In a chest region, the heat exchange material may have a smaller, tighter knit pattern that is firmer and provides structural support and an increased density of tubing for increasing temperature exchange. In some implementations, a region can include a hole or access point for a catheter to be inserted into the patient.

The different regions 802, 804, 806 can include variations of a particular interconnection pattern or each include an entirely different interconnection pattern. For example, the region 804 may include a weave pattern that is simpler, but that is stiffer and has less flexibility than a knit pattern, while region 802 includes a knit pattern allowing for greater conforming to patient contours. For example, neck and clavicle regions can include knit patterns (e.g., described in relation to FIGS. 1A-1E), while chest or body regions include weave or braided tube interconnection patterns.

Figure 9:
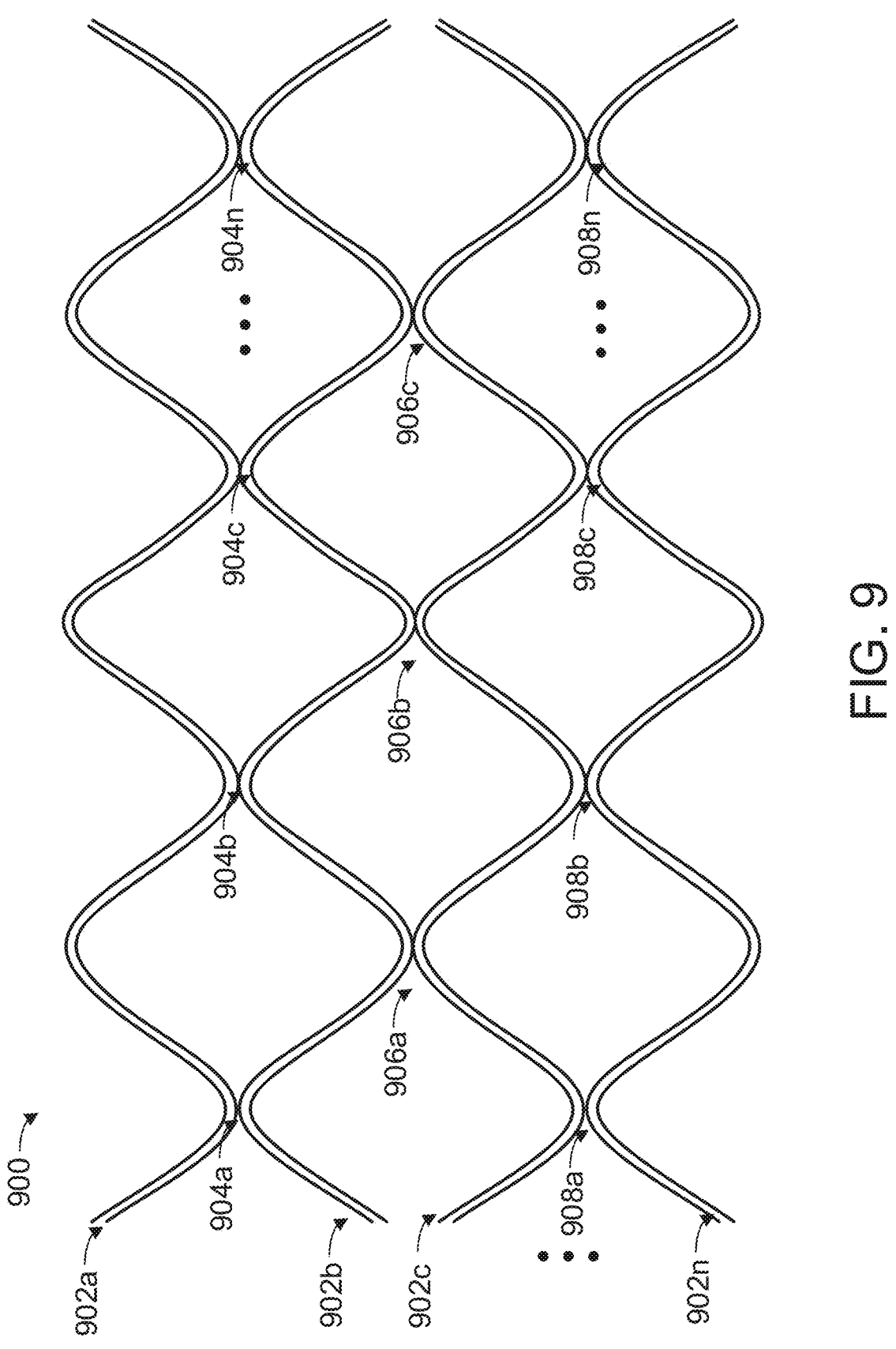
FIG. 9 shows an example of a material having a netted pattern.

FIG. 9 shows an example of a material 900, e.g., heat exchange material, having a netted pattern. The netted pattern of the material 900 can be an alternative or added to the knitted pattern of material 100. The netted pattern can be used on all or a portion of any of the heat exchange devices described herein, such as devices 110, 300, 400, 500, 600, 700, and 800. FIG. 9 shows a portion of heat exchange material 900.

The netted pattern of the material 900 can include portions 902a, 902b, 902c . . . 902n of a single tube or tubes 902a, 902b, 902c . . . 902n for a plurality of tubes. The portions 902 are coupled to one another or the tubes 902 are coupled to one another at intervals to allow for tube flexibility and heat exchange material flexibility. Portions or tubes 902a and 902b are coupled at points 904a, 904b, 904c . . . 904n. Portions or tubes 902b and 902c are coupled at points 906a, 906b, 906c . . . 906n. Portions or tubes 902c and 902n are coupled at points 908a, 908b, 908c . . . 908n.

The points 904, 906, and 908 at which the portions of a single tube or a plurality of tubes 902 are coupled to one another can be configured in different ways. In an example, the portions or tubes may be wrapped around one another to form a net. For example, at points 904*a-n*, tubes 902*a* and 902*b* are interlocked with one another. In combination with twisting or interlocking portions or tubes 902*a* and 902*b* at points 904, portions or tubes 902*b* and 902*c* are interlocked at points 906, creating a net. In some implementations, the coupling points 904, 906, 908 are formed by an adhesive to glue the portions or tubes 902 to one another, or coupled by any similar mechanical fastener including loops of fabric or material (e.g., cloth, rubber bands, etc.), clips, twist ties, and so forth. In some implementations, the distance between points 904, 906, and/or 908 can be varied to cause a variable netting pattern. The variable netting pattern can be used to increase or decrease a tube volume, and thus a heat exchange power, in a region of a patient. In some implementations, the variable netting pattern can also be used to create a material, garment or fabric with a topology matching that of a target region of patient anatomy.

Figure 10:
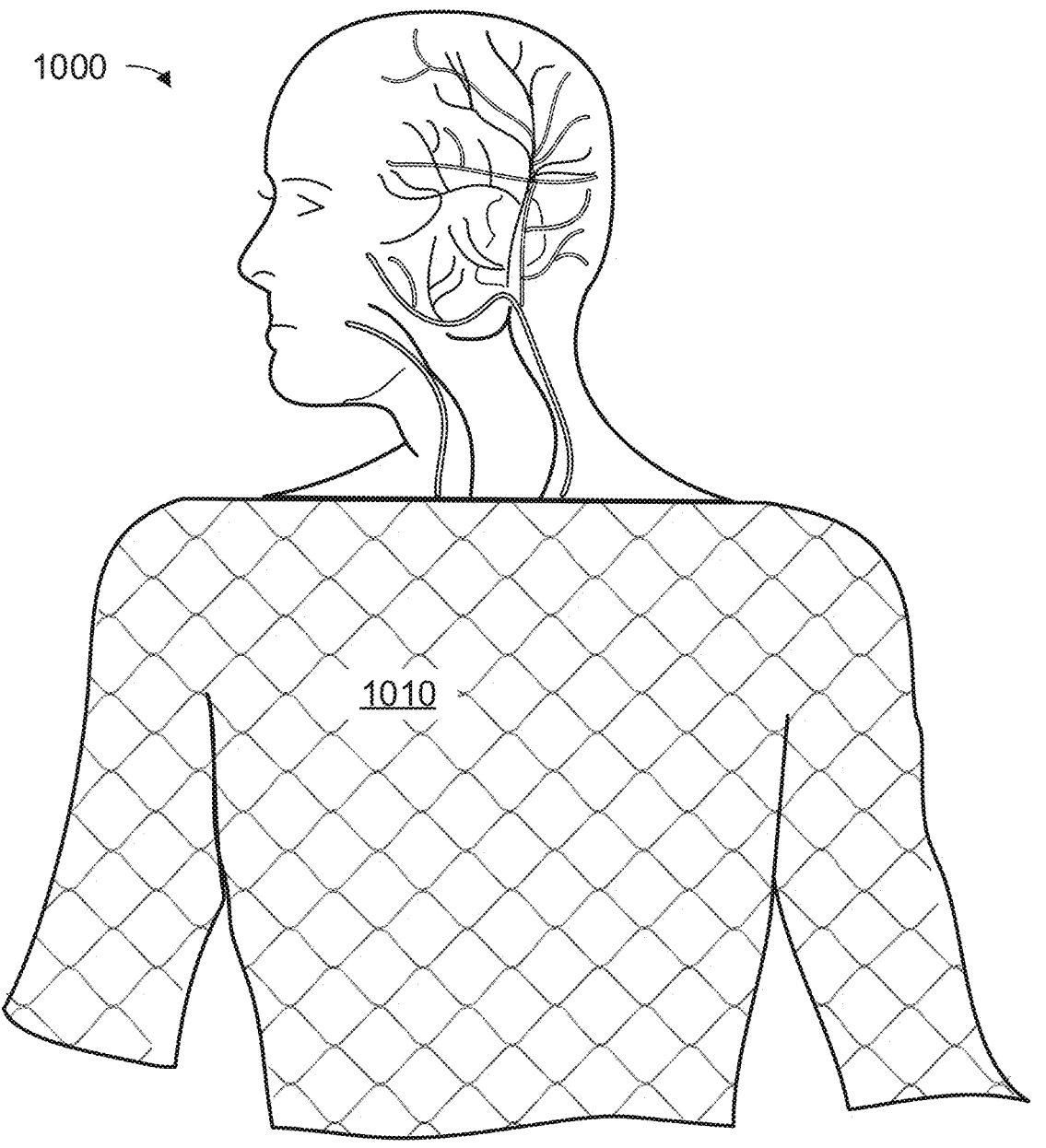
FIG. 10 shows an example heat exchange device having a netted pattern.

FIG. 10 shows an example heat exchange device 1000 having a netted pattern from material 900. Heat exchange device 1000 is similar to heat exchange device 600 previously described. Heat exchange device 1000 is configured to conform to the patient's body without substantial wrinkles, gaps, or folds.

Figure 11:
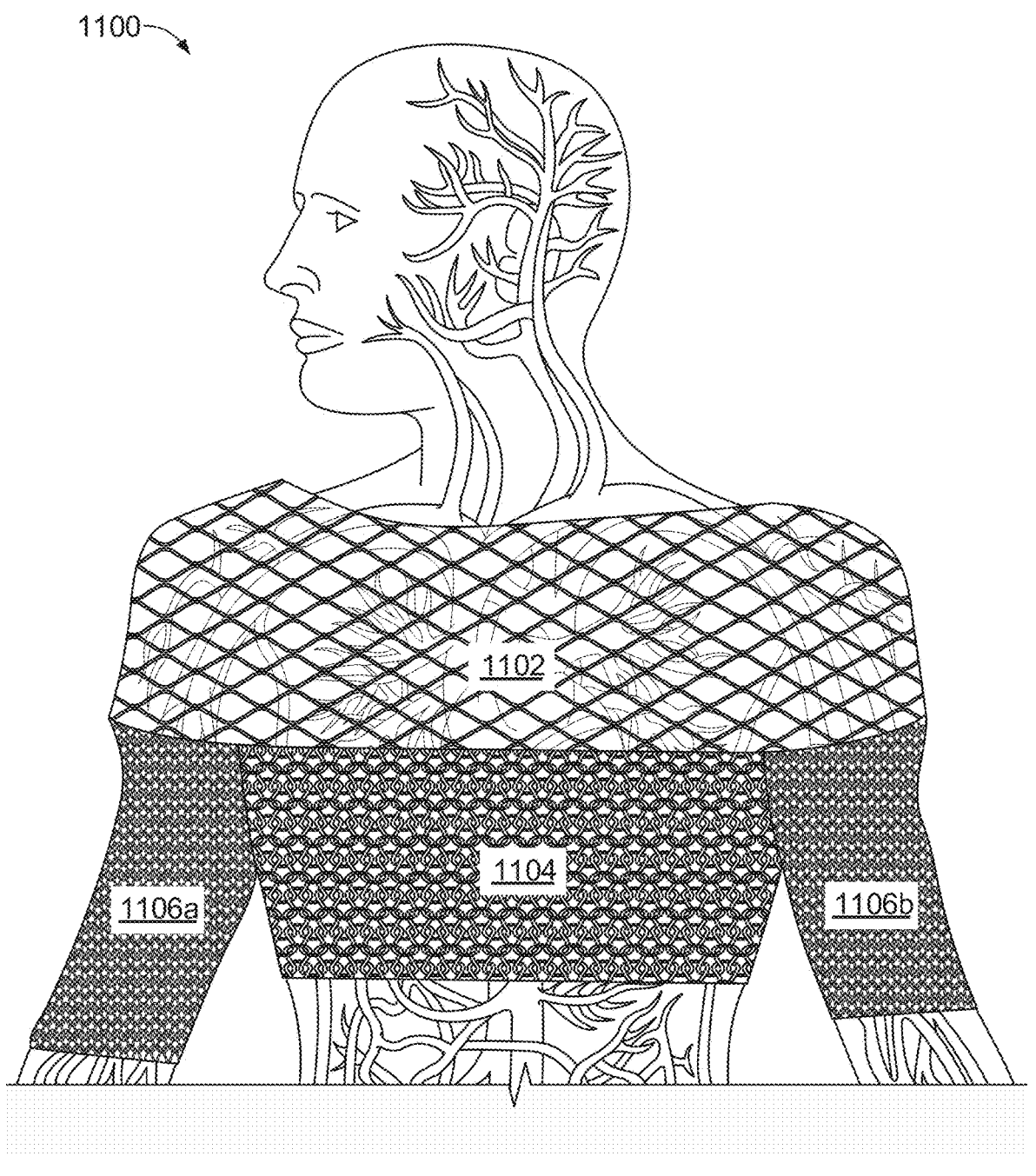
FIG. 11 shows an example heat exchange device including a plurality of tubing interconnection patterns.

FIG. 11 shows an example heat exchange device 1100 including a plurality of tubing interconnection patterns 1102, 1104, and 1106*a-b*. For example, pattern 1102 can be a netting pattern of material 900, while patterns 1104, 1106*a-b* can include knit patterns of material 100. While FIG. 11 shows a shirt heat exchange device 1110, any garment size or shape can include different tube interconnection patterns.

Figures 12A, 12B:
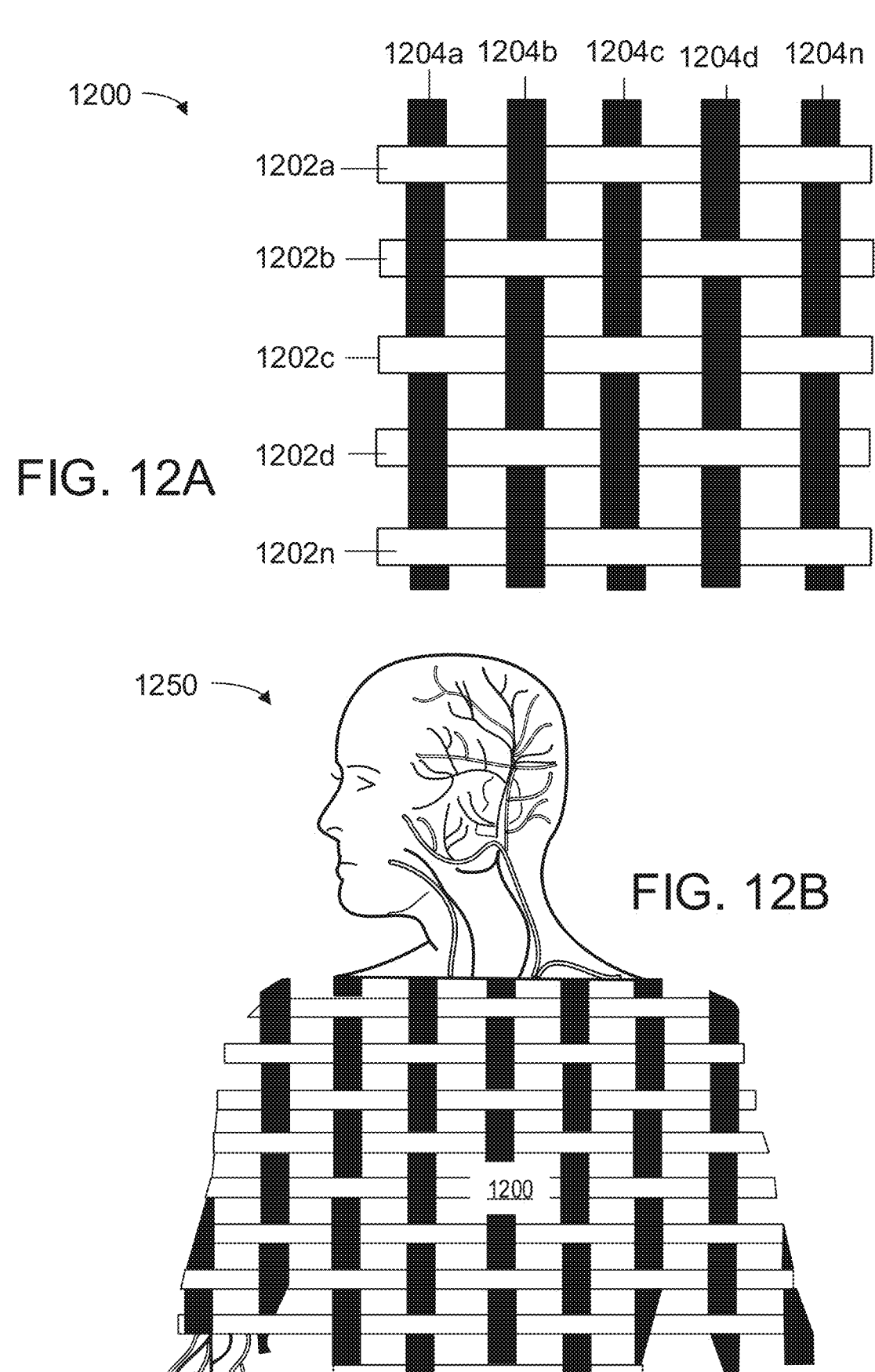
FIG. 12A shows an example of a material having a woven pattern.
FIG. 12B shows an example of a heat exchange device having a woven pattern.

FIG. 12A shows an example of a material 1200, e.g., heat exchange material, having a woven pattern. Tubes 1202*a-n* are along a first axis. Tubes 1204*a-n* are along a second, different axis. The tubes 1202 are woven with the tubes 1204. Alternatively, a single tube may be used, where first portions 1202*a-n* of the tube are woven with second portions 1204*a-n* of the tube. The woven pattern of material 1200 is less conformable in comparison with knitted pattern of heat exchange material 100. Generally, the woven pattern of material 1200 can be used as standalone heat exchange device (as shown in FIG. 12B) or in combination with other tube interconnection patterns when forming a garment.

FIG. 12B shows an example of a heat exchange device 1250 having a woven pattern of material 1200. The heat exchange device 1250 shows the entire device has having a woven pattern of material 1200. Generally, a portion of the heat exchange device 1250 includes a woven pattern in regions in which less flexibility or fewer contours are present. The woven pattern of material 1200 provides a simpler tube configuration and can be used in regions such as the back, chest, or torso of the patient.

FIG. 13 shows a flow diagram including an example process 1300 for forming a material, e.g., a heat exchange material. In some implementations, the process 1300 is for forming knitted pattern materials, such as material 100. The process 1300 includes obtaining (1302) a plurality of tubes, wherein at least one tube of the plurality of tubes has a lumen configured to receive fluid for flowing through the lumen of that tube. The process 1300 includes coupling (1304) the plurality of tubes together in a pattern to mechanically integrate the plurality of tubes together to form the conformable material or fabric wherein the conformable material or fabric is conformable into three dimensions. The process 1300 includes, for a series of locations along a first tube and a second tube of the plurality of tubes, performing the following operations. The process 1300 includes forming (1306) a first loop in the first tube of the plurality of tubes. The process 1300 includes forming (1308) a second loop in the second tube of the plurality of tubes. The process includes inserting (1310) the first loop through the second loop.

FIG. 14 shows a flow diagram including an example process 1400 for forming a material e.g., a heat exchange material. In some implementations, the process 1400 is for forming netted pattern e materials, such as material 900. The process 1400 includes obtaining (1402) a plurality of tubes, wherein at least one tube of the plurality of tubes has a lumen configured to receive fluid for flowing through the lumen of that tube. The process 1400 includes coupling (1404) the plurality of tubes together in a pattern to mechanically integrate the plurality of tubes together to form the conformable material or fabric wherein the conformable material or fabric is conformable into three dimensions. The process 1400 includes, for a series of locations along a first tube and a second tube of the plurality of tubes, performing the following operations. The process 1400 includes forming (1406) a first tube of the plurality of tubes into a series of peaks and valleys. The process 1400 includes wrapping (1408) a second tube of the plurality of tubes around the peaks of the first tube. The process 1400 includes wrapping (1410) a third tube of the plurality of tubes around the valleys of the first tube, where the first tube is between the second tube and the third tube. In an example, the netted pattern of material 900 of FIG. 9 is produced.

FIG. 15 shows a flow diagram including an example process 1500 for forming a material, e.g., a heat exchange material. In some implementations, the process 1500 is for forming netted pattern materials, such as material 900. The process 1500 includes obtaining (1502) a plurality of tubes, wherein at least one tube of the plurality of tubes has a lumen configured to receive fluid for flowing through the lumen of that tube. The process 1500 includes coupling (1504) the plurality of tubes together in a pattern to mechanically integrate the plurality of tubes together to form the conformable material or fabric wherein the conformable material or fabric is conformable into three dimensions. The process 1500 includes, for a series of locations along a first tube and a second tube of the plurality of tubes, performing the following operations. The process 1500 includes adhering (1506) a first tube of the plurality of tubes to a second tube of the plurality of tubes at each location of a first set of locations on the first tube. The process includes adhering (1508) the first tube of the plurality of tubes is to a third tube of the plurality of tubes at each location of a second set of locations on the first tube, wherein the locations of the first set of locations are alternating with the locations of the second set of locations.

FIG. 17 shows a flow diagram including an example process 1700 for forming a material, e.g., a heat exchange material. In some implementations, the process 1700 is for forming knitted pattern materials, such as material 100. The process 1700 includes obtaining (1702) at least one tube, wherein the at least one tube has a plurality of portions and a lumen configured to receive fluid for flowing through the lumen of the at least one tube. The process 1700 includes interconnecting (1704) the plurality of portions of the at least one tube with one another in a knit pattern to mechanically integrate the plurality of portions together to form the conformable material or fabric. The process 1700 includes, for a series of locations along a first portion and a second portion of the plurality of portions, performing the following operations. The process 1700 includes forming (1706) a first loop in the first portion. The process 1700 includes forming (1708) a second loop in the second portion. The process includes inserting (1710) the first loop through the second loop.

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, the processor of the temperature management system can be implemented using digital electronic circuitry, or in computer software, firmware, or hardware, or in combinations of one or more of them.

Some implementations described in this specification (e.g., the processor of the temperature management system, etc.) can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed for execution on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 16:
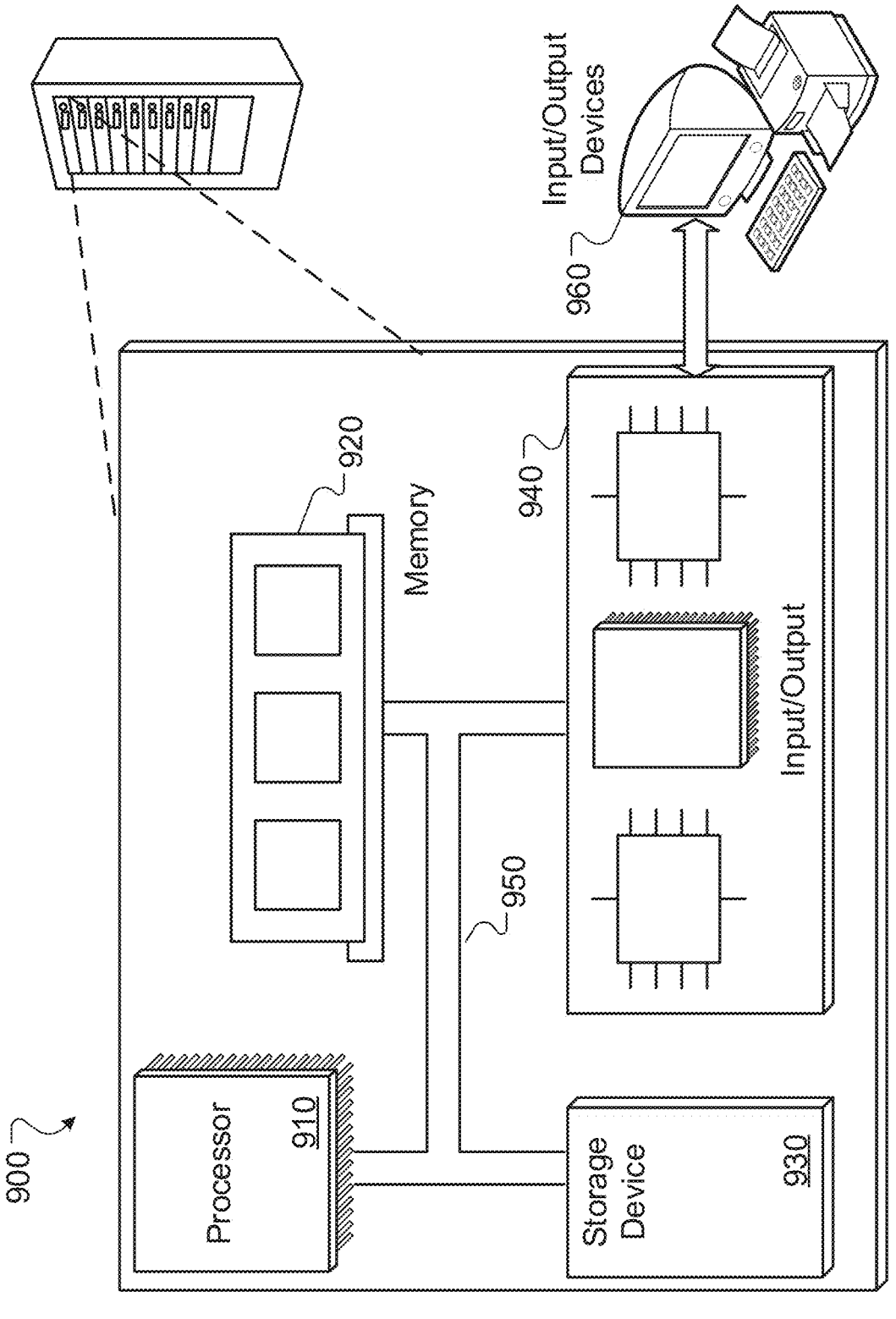
FIG. 16 is a diagram of an example computing system.

FIG. 16 shows an example computer system 1600 that includes a processor 1610, a memory 1620, a storage device 1630 and an input/output device 1640. Each of the components 1610, 1620, 1630 and 1640 can be interconnected, for example, by a system bus 1650. The processor 1610 is capable of processing instructions for execution within the system 1600. In some implementations, the processor 1610 is a single-threaded processor, a multi-threaded processor, or another type of processor. The processor 1610 is capable of processing instructions stored in the memory 1620 or on the storage device 1630. The memory 1620 and the storage device 1630 can store information within the system 1600.

The input/output device 1640 provides input/output operations for the system 1600. In some implementations, the input/output device 1640 can include one or more of a network interface device, e.g., an Ethernet card, a serial communication device, e.g., an RS-232 port, and/or a wireless interface device, e.g., an 802.11 card, a 3G wireless modem, a 4G wireless modem, a 5G wireless modem, etc. In some implementations, the input/output device can include driver devices configured to receive input data and send output data to other input/output devices, e.g., keyboard, printer and display devices 1660. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. For example, the detailed description and the accompanying drawings to which it refers are intended to describe some, but not necessarily all, examples or embodiments of the system. The described embodiments are to be considered in all respects only as illustrative and not restrictive. Nevertheless, various modifications may be made without departing from the scope of the data processing system described herein. Accordingly, other embodiments are within the scope of the following claims.

What is claimed is:

1. A system for providing external heat exchange to a patient, the system comprising:
    a heat exchange device for placement on the patient, the heat exchange device comprising:
    a plurality of tubes, at least one tube of the plurality of tubes having a lumen configured to receive fluid for flowing through the lumen to heat the tube or cool the tube;
    the plurality of tubes being interconnected into a pattern such that the plurality of interconnected tubes is configured to conform into a three dimensional shape, wherein each tube of the plurality of tubes comprises one or more loops, wherein a first loop of a first tube of the plurality of tubes is interlocked with a second loop of a second tube of the plurality of tubes; and
    a control console comprising:
    a pump configured to pump fluid through the at least one tube of the plurality of tubes;
    a heat exchanger in thermal communication with the fluid for flowing through the lumen of the at least one tube of the plurality of tubes to heat or cool the at least one tube;
    a controller configured to control operation of the pump; and
    a user interface configured to receive inputs for controlling the pump and to display operational data for operation of the pump.

2. The system of claim 1, further comprising:
    an intravenous catheter connected in series or in parallel with the heat exchange device.

3. The system of claim 1, further comprising:
    a cartridge configured to interface with the heat exchanger of the control console to exchange heat with the heat exchanger, the cartridge configured for fluid communication with the heat exchange device.

4. The system of claim 1, wherein the plurality of interconnected tubes form a conformable fabric or material that is conformable to a three dimensional surface.

5. The system of claim 1, wherein fluid flow in at least one tube of the plurality of tubes is configured to heat the tube or cool the at least one tube, and wherein the at least one tube is configured to perform heat transfer with an object in contact with the at least one tube, the heat transfer being based on the fluid flow through the at least one tube to heat or cool the at least one tube.

6. The system of claim 4, wherein the conformable fabric or material is comprised solely of the plurality of tubes.

7. The system of claim 1, wherein the plurality of tubes are interconnected in a conformable knit pattern, the conformable knit pattern being stretchable at least along a first axis in a first dimension and at least along a second axis in a second dimension.

8. The system of claim 7, wherein the conformable knit pattern comprises a first knit pattern for a first region of the conformable knit pattern and a second knit pattern for a second region of the conformable knit pattern, the first knit pattern being different than the second knit pattern.

9. The system of claim 7, wherein the conformable knit pattern comprises:
    the first tube of the plurality of tubes, the first tube having a series of peaks and valleys;
    the second tube of the plurality of tubes, the second tube configured to wrap around the peaks of the first tube; and
    a third tube of the plurality of tubes, the third tube configured to wrap around the valleys of the first tube, wherein the first tube is between the second tube and the third tube.

10. The system of claim 7, wherein the conformable knit pattern comprises one or more deformable cells configured to maintain an approximately constant perimeter during deformation.

11. The system of claim 7, wherein the conformable knit pattern comprises interlocking loops of a plurality of sizes.

12. The system of claim 1, wherein the first tube comprises a plurality of loops, the plurality of loops comprising loops having different sizes from one another.

13. The system of claim 1, further comprising a pump tube that is configured to interface with the pump, the pump tube being connected to the at least one tube of the plurality of tubes in a closed loop.

14. The system of claim 13, wherein the pump is a peristaltic pump configured to drive fluid through the pump tube and the at least one tube of the plurality of tubes.

15. The system of claim 1, wherein the plurality of interconnected tubes form a conformable fabric or material, wherein the fabric or material comprises edge pieces, or the tubing of the plurality of interconnected tubes forms edging of the fabric or material.

16. A wearable heat-exchange device comprising:
    a plurality of tubes, at least one tube of the plurality of tubes having a lumen configured to receive fluid, the at least one tube configured to allow for fluid flow through the lumen, the plurality of tubes being interconnected into a pattern such that the plurality of interconnected tubes is configured to conform into a wearable three-dimensional shape, wherein each tube of the plurality of tubes comprises one or more loops, wherein a first loop of a first tube of the plurality of tubes is interlocked with a second loop of a second tube of the plurality of tubes.

17. The device of claim 16, wherein the plurality of interconnected tubes form a conformable fabric or material that is conformable to a three dimensional surface.

18. The device of claim 17, wherein the conformable fabric or material is comprised solely of the plurality of tubes.

19. The device of claim 16, wherein fluid flow in at least one tube of the plurality of tubes is configured to heat or cool the at least one tube, and wherein the at least one tube is configured to perform heat transfer with an object in contact with the at least one tube, the heat transfer being based on the fluid flow through the at least one tube.

20. A wearable heat-exchange device comprising:

a plurality of tubes, at least one tube of the plurality of tubes having a lumen configured to receive fluid, the at least one tube configured to allow for fluid flow through the lumen, the plurality of tubes being interconnected into a pattern such that the plurality of interconnected tubes is configured to conform into a wearable three-dimensional shape, wherein the plurality of tubes is interconnected in a conformable knit pattern, the conformable pattern being stretchable at least along a first axis in a first dimension and at least along a second axis in a second dimension, wherein the conformable knit pattern comprises a first knit pattern for a first region of the conformable knit pattern and a second knit pattern for a second region of the conformable knit pattern, the first knit pattern being different than the second knit pattern.

* * * * *